US010076311B2

(12) United States Patent
Oh et al.

(10) Patent No.: US 10,076,311 B2
(45) Date of Patent: *Sep. 18, 2018

(54) METHOD AND APPARATUS FOR REGISTERING MEDICAL IMAGES

(71) Applicant: SAMSUNG ELECTRONICS CO., LTD., Suwon-si (KR)

(72) Inventors: Youngtaek Oh, Seoul (KR); Jungbae Kim, Seoul (KR); Jayeon Jeong, Yongin-si (KR); Youngkyoo Hwang, Seoul (KR); Wonchul Bang, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 684 days.

This patent is subject to a terminal disclaimer.

(21) Appl. No.: 14/605,125

(22) Filed: Jan. 26, 2015

(65) Prior Publication Data
US 2015/0209015 A1    Jul. 30, 2015

(30) Foreign Application Priority Data

Jan. 24, 2014 (KR) .......... 10-2014-0009176
Jan. 8, 2015 (KR) .......... 10-2015-0002858

(51) Int. Cl.
*A61B 8/08* (2006.01)
*A61B 8/00* (2006.01)

(52) U.S. Cl.
CPC .......... *A61B 8/5261* (2013.01); *A61B 8/4245* (2013.01); *A61B 8/463* (2013.01)

(58) Field of Classification Search
CPC ......... A61B 8/5261; A61B 8/14; A61B 8/463; A61B 8/4245; A61B 8/0825
See application file for complete search history.

(56) References Cited

U.S. PATENT DOCUMENTS

| | | |
|---|---|---|
| 8,150,498 B2 | 4/2012 | Gielen et al. |
| 8,290,303 B2 | 10/2012 | Washburn et al. |
| 8,320,711 B2 | 11/2012 | Altmann et al. |
| 8,345,943 B2 | 1/2013 | Neemuchwala et al. |
| 8,447,384 B2 | 5/2013 | Xu et al. |
| 2007/0010743 A1* | 1/2007 | Arai .................. A61B 8/12 600/443 |
| 2010/0135546 A1 | 6/2010 | Cziria |

FOREIGN PATENT DOCUMENTS

KR    10-1121286 B1    3/2012

OTHER PUBLICATIONS

Lindseth, thesis, Ultrasound Guided Surgery: Multimodal Visualization and Navigation Accuracy, Norwegian University of Science and Technology, Dec. 2002.*

* cited by examiner

*Primary Examiner* — Bo J Peng
(74) *Attorney, Agent, or Firm* — Sughrue Mion, PLLC

(57) ABSTRACT

An apparatus for registering medical images includes a processor configured to acquire, via an ultrasound probe, a first cross-section of a first medical image, the first cross-section comprising a reference point of an object; and a memory configured to store a second medical image. The processor is configured to obtain a second cross-section of the second medical image corresponding to the first cross-section by using the reference point, and register the first and second medical images with each other.

32 Claims, 15 Drawing Sheets

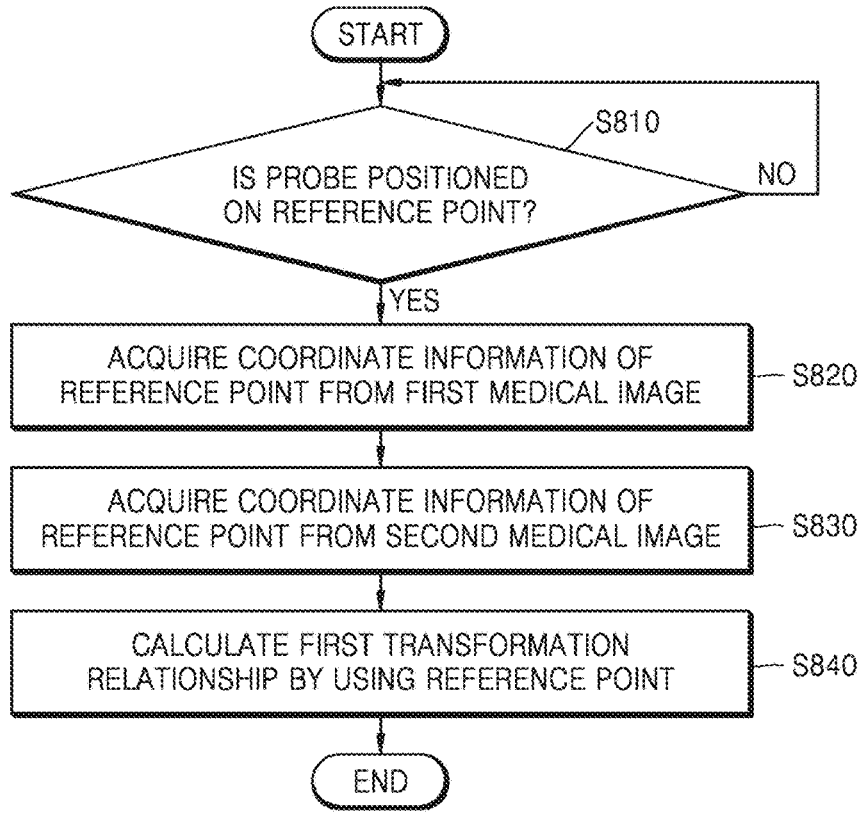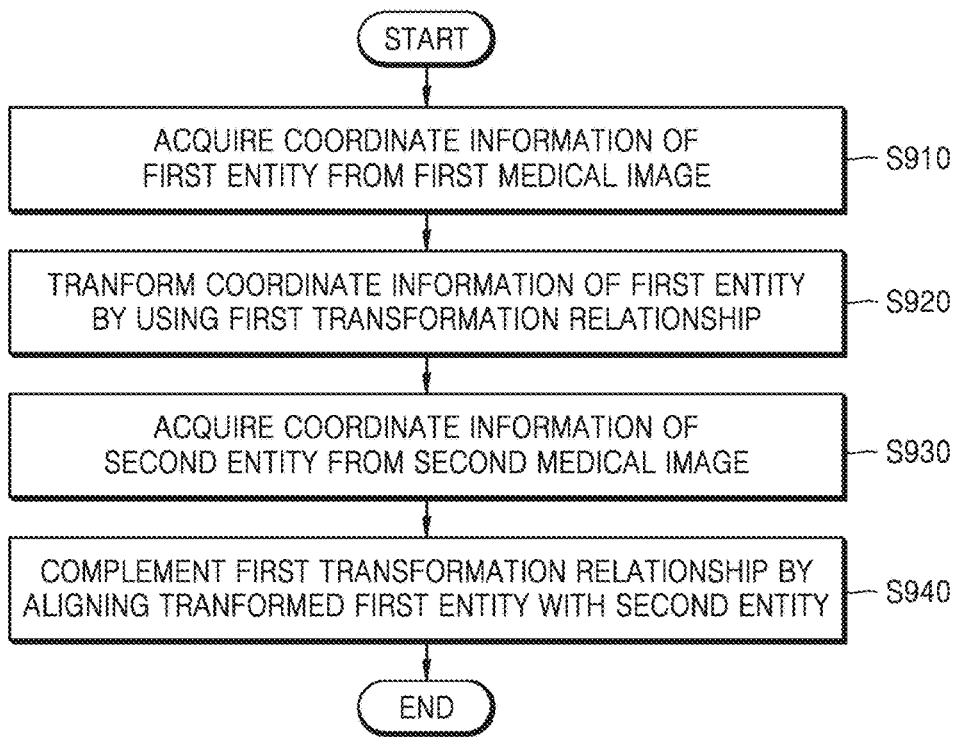

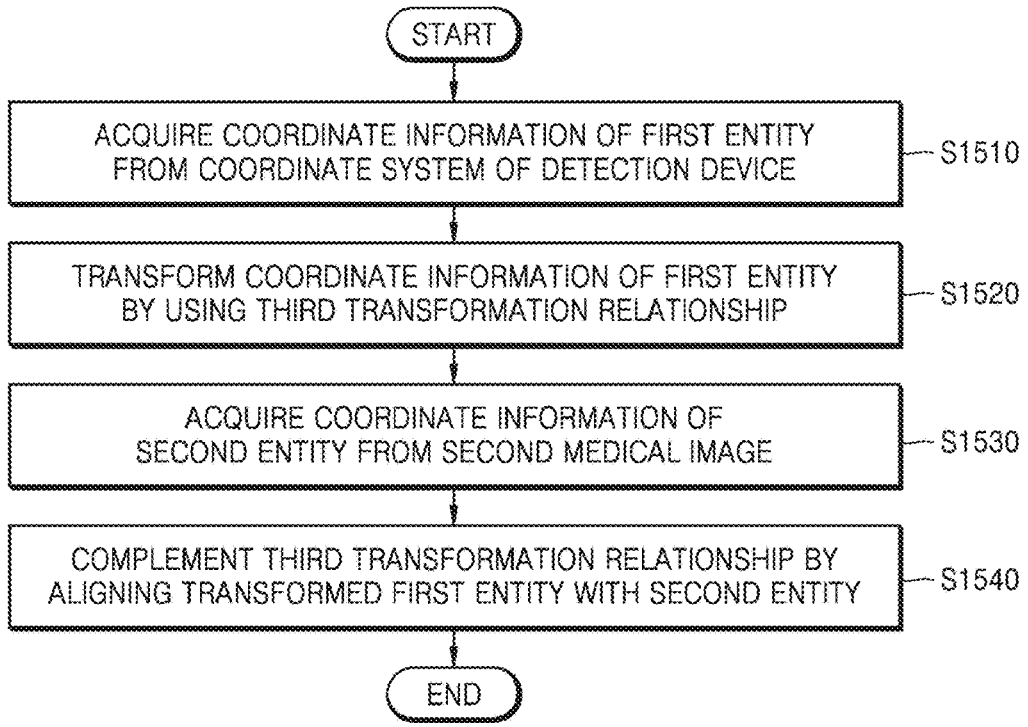
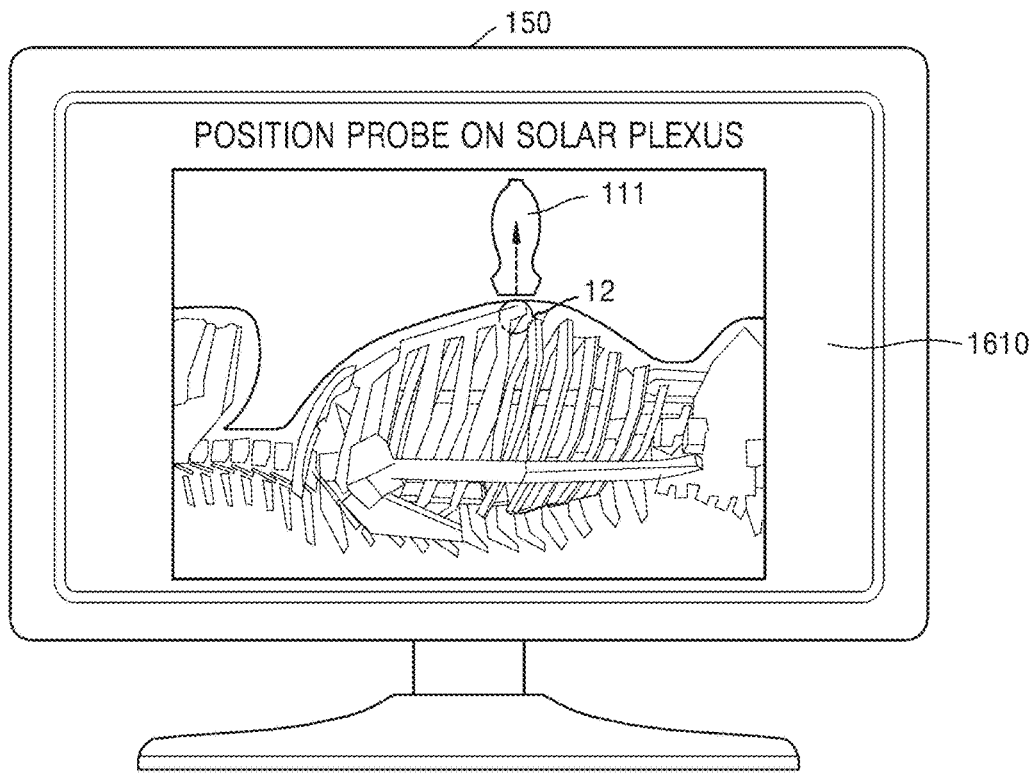

METHOD AND APPARATUS FOR REGISTERING MEDICAL IMAGES

CROSS REFERENCE TO RELATED APPLICATIONS

This application claims priority from Korean Patent Application Nos. 10-2014-0009176, filed on Jan. 24, 2014, and 10-2015-0002858, filed on Jan. 8, 2015, in the Korean Intellectual Property Office, the disclosures of which are incorporated herein in their entireties by reference.

BACKGROUND

1. Field

Apparatuses and methods consistent with exemplary embodiments relate to registering medical images of different modalities.

2. Description of the Related Art

Due to advancement in medical technologies, medical images having a high resolution may be obtained. With emergence of medical devices utilizing micromanipulation, a technique for treating a living body without direct incision for exposing a portion to be treated is being developed. The technique involves cutting a hole to a minimum size on a living body and inserting a catheter or a medical needle into a blood vessel or other desired portion of the living body while observing the interior regions of the living body by using medical imaging equipment. This method is called an image-guided surgery or an interventional surgical procedure.

According to the above method, an operator may identify positions of organs or lesions by using images. Furthermore, while performing an operation, an operator detects changes in positions of organs associated with a patient's respiration or movement. Thus, the operator needs to accurately and quickly detect a patient's respiration or movement based on real-time ultrasound images in order to perform an operation. However, it may be difficult to identify the shapes of organs and lesions in the real-time ultrasound images with a naked eye.

Unlike ultrasound images, magnetic resonance (MR) images or computed tomography (CT) images may be used to clearly distinguish organs and lesions. However, since magnetic resonance imaging (MRI) or CT equipment is not able to acquire images in real-time, a patient's respiration or movement that occurs during a medical procedure cannot be detected in MR or CT images.

Thus, there is a need to register a medical image captured in real-time in association with a medical image of a different modality from that of the real-time image. In order to register a plurality of medical images of different modalities, feature points extracted from each medical image may be used. However, according to this method, image registration may be difficult due to the inadequate quality of medical images.

SUMMARY

One or more exemplary embodiments provide methods and apparatuses for registering a plurality of medical images with different modalities.

Additional aspects will be set forth in part in the description which follows and, in part, will be apparent from the description, or may be learned by practice of the presented embodiments.

According to an aspect of an exemplary embodiment, an apparatus for registering medical images includes: a memory configured to store a second medical image; and a processor configured to acquire via a probe a first cross-section of a first medical image and obtain a second cross-section of the second medical image corresponding to the first cross-section from the memory by using a reference point of an object, thereby registering the first and second medical images with each other.

The processor may register the first medical image with the second medical image in response to a first user command for positioning the probe on the reference point of the object.

The apparatus for registering medical images further may include a controller configured to determine whether the first user command is input by using at least one selected from the first medical image, a result of detection of movement of the probe, and results of input via a user interface configured to receive a user command.

When a second user command for image registration is input via the user interface and coordinate information of the reference point can be obtained from a cross-section of the first medical image, the controller may determine that the first user command is input.

When the probe does not move for a predetermined time while the coordinate information of the reference point can be obtained from a cross-section of the first medical image, the controller may determine that the first user command input.

The reference point may be at least one of an entity of the object that remains undeformed despite a respiration and an entity of the object that is distinguishable with the naked eye.

The entity may be one selected from a bone, a belly button, and a superior mesenteric artery.

The bone may be a solar plexus.

The first cross-section may be acquired when an axis of the probe is disposed parallel to an axis of the object.

The axis of the probe may be parallel to a coordinate axis of the first medical image.

The axis of the object may be parallel to a coordinate axis of the second medical image.

The processor may calculate one of a first transformation relationship between coordinate systems of the first and second medical images by using the reference point and a second transformation relationship between a coordinate system of a detection device for detecting a position and an orientation of the probe and the coordinate system of the second medical image and extracts the second cross-section from the second medical image by using the one of the first and second transformation relationships.

The processor may acquire first coordinate information and second coordinate information of the reference point from the coordinate system of the first medical image and the coordinate system of the second medical image, respectively, and calculates the first transformation relationship by transforming the first coordinate information into the second coordinate information.

The processor may complement the first or the second transformation relationship by aligning a first entity in the first medical image with a second entity in the second medical image.

The processor may acquire third coordinate information and fourth coordinate information of the reference point from the coordinate system of the detection device and the coordinate system of the second medical image, respectively, and calculates the second transformation relationship by transforming the third coordinate information into the fourth coordinate information.

The processor may acquire a third cross-section of the first medical image corresponding to movement of the probe via the probe and obtains a fourth cross-section of the second medical corresponding to the third cross-section by using the one of the first and second transformation relationships.

The movement of the probe may be a change in at least one of the position and the orientation of the probe.

According to an aspect of another exemplary embodiment, a method of registering medical images includes: acquiring via a probe a first cross-section of a first medical image; and obtaining a second cross-section of a second medical image corresponding to the first cross-section from the second medical image by using a reference point of an object.

The obtaining of the second cross-section may be performed in response to a user command for positioning the probe on the reference point of an object.

The reference point may be at least one of an entity of the object that remains undeformed despite a respiration and an entity of the object that is distinguishable with the naked eye.

The entity the entity may be one selected from a bone, a belly button, and a superior mesenteric artery.

The method of registering medical images further may include: displaying an indicator for explaining the reference point.

The method of registering medical images further may include: displaying a list of candidates for the reference point; and receiving a user command for selecting one candidate from the list as the reference point.

According to an aspect of another exemplary embodiment, an apparatus for registering medical images includes; a communicator configured to receive a first medical image and a second medical image, the second medical image having a different modality from that of the first medical image; and a processor configured to register the first and second medical images, wherein, when an ultrasound probe is disposed at a reference point of an object to obtain a first cross-section of the first medical image, the processor is configured to automatically obtain a second cross-section of the second medical image corresponding to the first cross-section, by using the reference point.

The first medical image may be captured in real-time and the second medical image is captured before the first medical image.

The processor may be configured to calculate a transformation relationship to transform coordinates of the reference point in the first medical image to coordinates of the reference point in the second medical image, and extract the second cross-section using the transformation relationship.

The processor may be configured to complement the transformation relationship by matching a first entity, of which coordinate information being transformed by using the transformation relationship, in the first medical image to coordinate information of a second entity in the second medical image.

The processor may be configured to complement the transformation relationship by matching a geometry between a first entity, of which coordinate information being transformed by using the transformation relationship, in the first medical image and a second entity in the second medical image to a pre-stored geometry.

The communicator may further be configured to receive coordinates of the ultrasound probe, and the processor is configured to calculate a transformation relationship to transform the coordinates of the ultrasound probe to coordinates of the reference point in the second medical image, and extract the second cross-section using the transformation relationship.

When the coordinates of the ultrasound probe are changed, the processor may be configured to obtain a third cross-section of the second medical image by using the transformation relationship.

The apparatus further may include: a display configured to display the first cross-section of the first medical image and the second cross-section of the second medical image.

The display may be configured to at least one of display the first cross-section and the second cross-section on separate areas of a screen and display an image obtained by fusing the first cross-section and the second cross-section.

According to an aspect of another exemplary embodiment, an apparatus for registering medical images includes: a communicator configured to receive a first medical image and a second medical image, the second medical image having a different modality from that of the first medical image; and a processor configured to register the first and second medical images, wherein, when an ultrasound probe is disposed at a reference point of an object to obtain a first cross-section of the first medical image, the processor is configured to automatically obtain a second cross-section of the second medical image corresponding to the first cross-section, by using the reference point.

The first medical image may be captured in real-time and the second medical image is captured before the first medical image.

The processor may be configured to calculate a transformation relationship to transform coordinates of the reference point in the first medical image to coordinates of the reference point in the second medical image, and extract the second cross-section using the transformation relationship.

The processor may be configured to complement the transformation relationship by matching a first entity, of which coordinate information being transformed by using the transformation relationship, in the first medical image to coordinate information of a second entity in the second medical image.

The processor may be configured to complement the transformation relationship by matching a geometry between a first entity, of which coordinate information being transformed by using the transformation relationship, in the first medical image and a second entity in the second medical image to a pre-stored geometry.

The communicator may further be configured to receive coordinates of the ultrasound probe, and the processor is configured to calculate a transformation relationship to transform the coordinates of the ultrasound probe to coordinates of the reference point in the second medical image, and extract the second cross-section using the transformation relationship.

When the coordinates of the ultrasound probe are changed, the processor may be configured to obtain a third cross-section of the second medical image by using the transformation relationship.

The apparatus further may include: a display configured to display the first cross-section of the first medical image and the second cross-section of the second medical image.

The display may be configured to at least one of display the first cross-section and the second cross-section on separate areas of a screen and display an image obtained by fusing the first cross-section and the second cross-section.

BRIEF DESCRIPTION OF THE DRAWINGS

The above and/or other aspects will become more apparent by describing certain exemplary embodiments with reference to the accompanying drawings, in which:

FIG. 8 is a flowchart of a method of calculating a first transformation relationship by using a reference point by a registration device, according to an exemplary embodiment;

FIG. 9 is a flowchart of a method of complementing a first transformation relationship according to an exemplary embodiment;

FIG. 15 is a flowchart of a method of complementing a third transformation relationship according to an exemplary embodiment;

FIG. 16 is a diagram for explaining a method of displaying an indicator for indicating a reference point, according to an exemplary embodiment.

DETAILED DESCRIPTION

Figure 1:
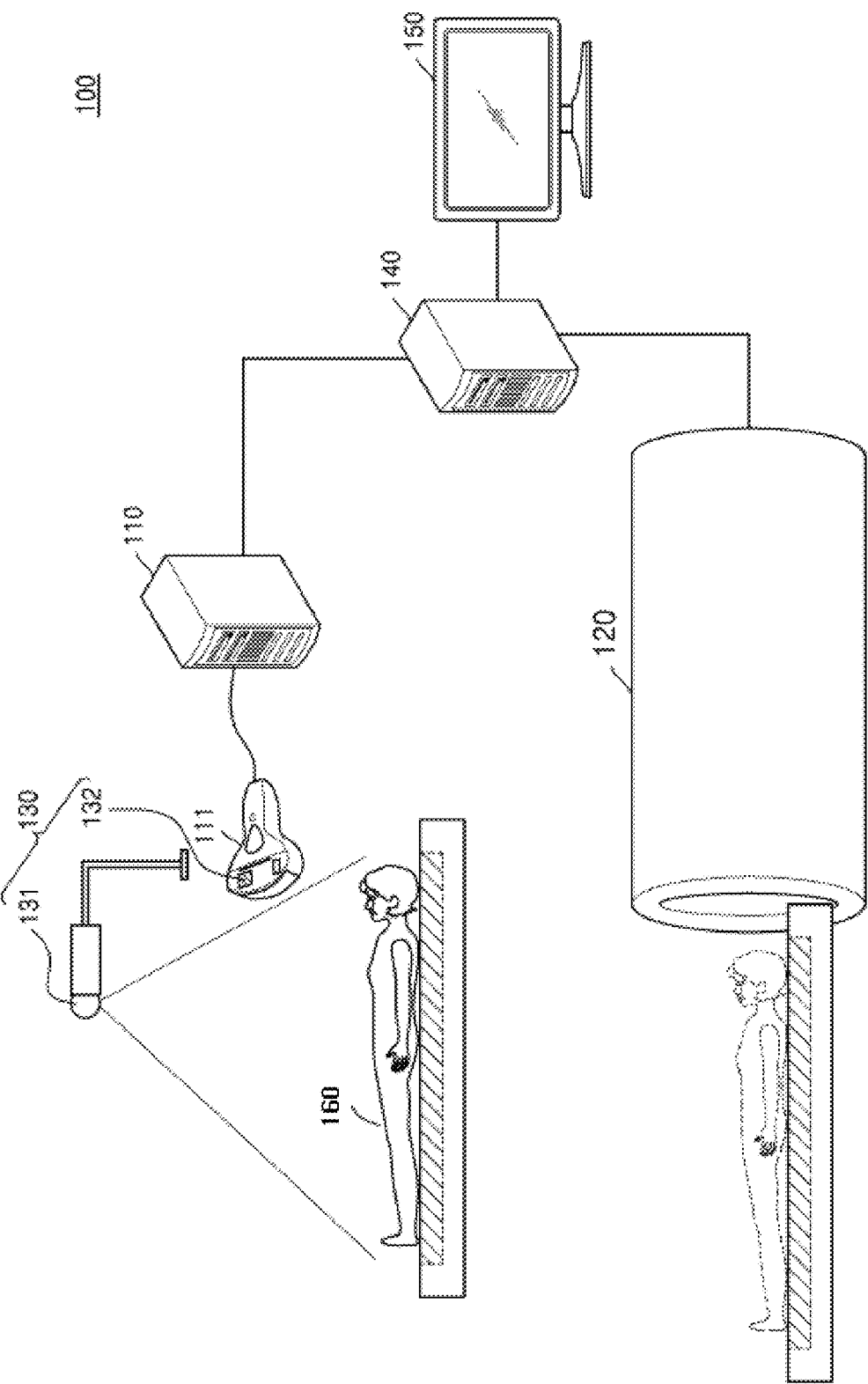
FIG. 1 illustrates a medical imaging system according to an exemplary embodiment.

Certain exemplary embodiments are described in greater detail below with reference to the accompanying drawings. In the drawings, reference numerals refer to like elements throughout, and repeated descriptions thereof are omitted to avoid redundancy. Expressions such as "at least one of," when preceding a list of elements, modify the entire list of elements and do not modify the individual elements of the list.

In the present specification, an "object" may include a person or an animal, or a part of a person or an animal. For example, the object may include the liver, the heart, the womb, the brain, a breast, the abdomen, or a blood vessel. Furthermore, a "user" refers to a medical professional, such as a doctor, a nurse, a medical laboratory technologist, a medical imaging expert, and an engineer who repairs a medical apparatus, but the user is not limited thereto.

FIG. 1 illustrates a medical imaging system 100 according to an exemplary embodiment. Referring to FIG. 1, the medical imaging system 100 according to an exemplary embodiment includes a first medical device 110, a second medical device 120, a detection device 130, a registration device 140, and a display 150.

The first and second medical devices 110 and 120 respectively generate first and second medical images and provide the first and second medical images to the registration device 140. The first and second medical images have different modalities. In other words, the first and second medical images are generated in different methods and based on different principles. The registration device 140 acquires the first and second medical images of different modalities and registers the first and second medical images in association with each other. The display 150 may display an image obtained from the registration device 140.

The first medical device 110 provides in real-time a first medical image of a volume of interest (VOI) in an object 160. For example, if deformation and/or displacement of an organ occurs due to a physical activity of the object 160, the first medical image may change in real-time. However, it may be difficult to clearly observe all organs and lesions in the object 160 in the first medical image. Also, it may be difficult to detect deformation and/or displacement of an organ only with the first medical image.

In an exemplary embodiment, the first medical device 110 may be an ultrasonography machine that generates an image in real-time while performing an interventional medical procedure on a patient. The first medical device 110 is not limited thereto, and may be another medical device such as an optical coherence tomography (OCT) machine for providing an image in real-time.

When the first medical device 110 is an ultrasonography machine, the first medical device 110 generates an ultrasound image by using a probe 111 that transmits ultrasound waves to the object 160 and detects ultrasound waves reflected from the object 160. The probe 111 may include a piezoelectric transducer, but is not limited thereto. Alternatively, the probe 111 may include a capacitive micromachined ultrasonic transducer (cMUT) for converting ultrasound waves into electrical signals and vice versa due to a change in capacitance, a magnetic micromachined ultrasonic transducer (mMUT) for converting ultrasound waves into electrical signals and vice versa due to a change in a magnetic field, or an optical ultrasonic detector for converting ultrasound waves into electrical signals and vice versa due to a change in optical properties.

When an ultrasound wave having a frequency in the range of several megahertz (MHz) to several hundreds of MHz are transmitted to a specified portion inside a patient's body, the ultrasound waves are partially reflected from layers between different tissues. Ultrasound waves are reflected from entities that undergo a density change within a body, such as blood cells in blood plasma and small structures in organs.

The reflected ultrasound waves vibrate a transducer in the probe 111, and the transducer converts the vibrations into electrical pulses. The electrical pulses are then transformed into an image. If entities have different ultrasound reflection characteristics, the entities may be represented as different brightness values in a brightness (B)-mode ultrasound image.

The second medical device 120 generates a second medical image of a VOI in an object in a non-real-time manner.

The second medical image may be captured in advance before a medical procedure is performed when the non real-time properties of the second medical device 120 are considered.

For example, the second medical device 120 may be at least one of a computed tomography (CT) apparatus, a magnetic resonance imaging (MRI) apparatus, an X-ray apparatus, a single photon emission computed tomography (SPECT) apparatus, and a positron emission tomography (PET) apparatus. For convenience of explanation, it is hereinafter assumed that the second medical image is a magnetic resonance (MR) or CT image, but the second medical image is not limited thereto.

A CT or MR image generated by the second medical device 120 may clearly identify the positions of organs or lesions. However, since organs may be deformed or positions of the organs may be changed when a patient moves (e.g., takes a breath, tosses or turns) during an imaging operation, it may be difficult to detect real-time deformation and displacement of organs caused by the patient's movement in the CT or MR image.

The second medical device 120 does not output an image in real-time. When the image is a CT image, a patient and an operator may have a risk of being exposed to radiation for a long time because the CT image is produced by using the radiation. Thus, short-time imaging may be desirable. If the image is an MR image, it may take a long time to capture a single image. The CT image is imaged when a patient temporarily holds his or her breath, e.g., by inhaling the breath to a maximum.

Medical images imaged by the first or second medical device 110 or 120 may be two-dimensional (2D) cross-sectional images or a three-dimensional (3D) image created by accumulating 2D cross-sectional images. For example, the first medical device 110 may generate 2D cross-sectional images, or produce a 3D image by hand sweeping or wobbling the probe 111 or by using the probe 111 having a 2D array.

The second medical device 120 also captures a plurality of cross-sections by changing a location or orientation of an object or the second medical device 120. The cross-sections are stacked to form a 3D volume image data that represents a specified portion of a patient's body in a 3D manner, which is called a multiplanar reconstruction (MPR). The second medical image may be a contrast-enhanced image showing a patient's organ of interest with an improved brightness. It is hereinafter assumed for convenience of explanation that medical images are 2D or 3D images.

The detection device 130 may detect the movement of the probe 111 by detecting at least one of a position and an orientation of the probe 111. The detection device 130 may include a magnetic field generator 131 and a sensor 132 for sensing a change in a magnetic field. The magnetic field generator 131 may be fixed to a specified position of the first medical device 110 or mounted on the probe 111. For example, the magnetic field generator 131 may be fixed at a certain location of the first medical apparatus 110, and the sensor 132 may be disposed on the probe 111, or vice versa. Thus, the detection device 130 may detect at least one of a position and an orientation of the probe 111 from a relative position of the magnetic field generator 131 with respect to the sensor 132. The detection device 130 may further include an optical sensor, an accelerometer sensor, or a slope sensor for detecting at least one of a position and an orientation of the probe 111. The detection device 130 may calculate at least one of a position and an orientation of the probe 111 as coordinate information of the detection device 130 in a coordinate system.

The registration device 140 registers the first medical image acquired by the first medical device 110 with the second medical image acquired by the second medical device 120. The registration of the first and second medical images may include a corresponding transformation relationship between a coordinate system of the first medical image and a coordinate system of the second medical image. A cross-section of the first medical image is in a one-to-one correspondence with a position and an orientation of the probe 111.

According to an exemplary embodiment, when the probe 111 is located at a specific position and in a specific orientation, the medical imaging system 100 may calculate a transformation relationship for registering the first medical image with the second medical image. Registration of the first and second medical images may be performed using at least one of information about a position and an orientation of the probe 111 and coordinate information of entities in the first and second medical images. This registration method may require less extensive anatomical knowledge about an object, compared to an image registration based on only movement of the probe 111, detected by the detection device 130. The method may also reduce an error occurring from an image registration compared to an image registration based on an entity in an image. The information about the position and the orientation of the probe 111 may also be represented as coordinate information of the probe 111. Hereinafter, the information about the position and the orientation of the probe 111 and the coordinate information of the probe 111 are interchangeably used.

According to an exemplary embodiment, the registered image may be a fusion image obtained by fusing the first and second medical images. In another exemplary embodiment, the registered image may be an image in which the first and second medical images captured at the same observation point are disposed parallel to each other. The registered image may be displayed on the display 150.

Although the first medical device 110, the detection device 130, the registration device 140, and the display 150 are illustrated as separate devices, it is only for convenience of explanation, and some or all of the first medical device 110, the detection device 130, and the display 150 may be integrated into a single device.

To acquire a cross-section of the second medical image corresponding to a cross-section of the first medical image, the registration device 140 may acquire a first transformation relationship between coordinate systems of the first and second medical images. To easily acquire the first transformation relationship therebetween, at least one of a position and an orientation of the probe 111 may be used because the cross-section of the first medical image is in a one-to-one correspondence with the position and the orientation of the probe 111.

Figure 2:
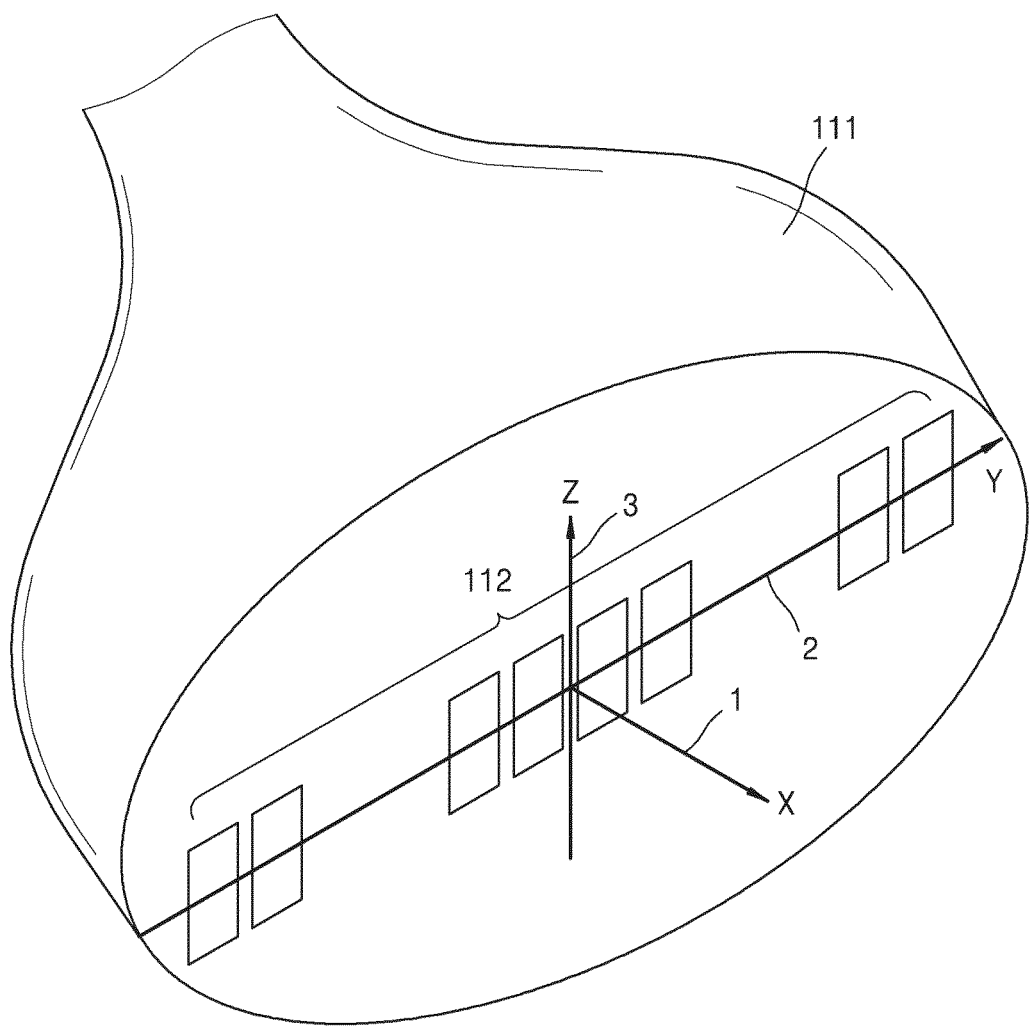
FIG. 2 is a diagram for explaining an axis of a probe according to an exemplary embodiment.

FIG. 2 is a diagram for explaining an axis of the probe 111 according to an exemplary embodiment. Referring to FIG. 2, the axis of the probe 111 is defined by a first axis (or an X-axis) 1 that is an axial direction defined as a direction of propagation of a transmitted ultrasound wave with respect to a transducer 112 of the probe 111, a second axis (or a Y-axis) 2 that is a lateral direction defined as a width direction of the transducer 112, and a third axis (or a Z-axis) 3 that is an elevation direction defined as a height direction of the transducer 112. A center of the probe 111 is a center of an array of transducers 112, and the position of the probe 111 may be a position of the center of the probe 111.

Figure 3:
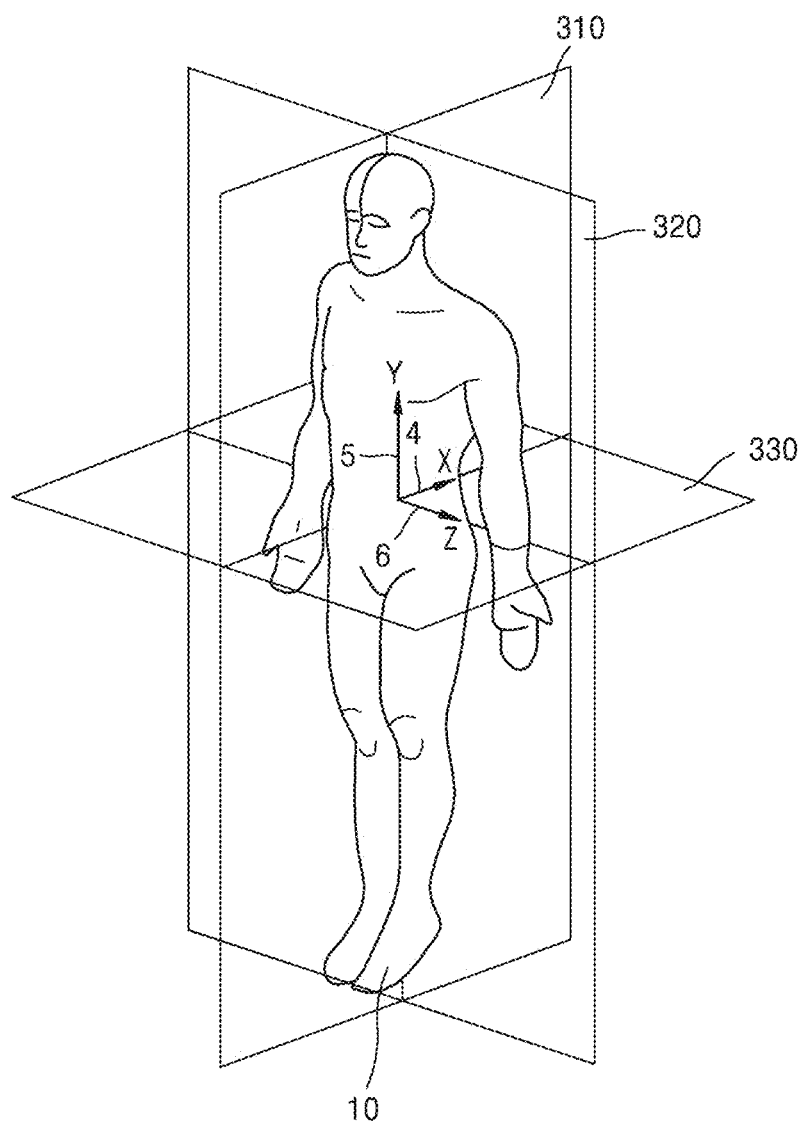
FIG. 3 is a diagram for explaining an axis of an object according to an exemplary embodiment.

FIG. 3 is a diagram for explaining an axis of an object according to an exemplary embodiment. Referring to FIG. 3, planes cut across an object 10 may include a sagittal plane 310, a coronal plane 320, and a transverse plane 330. The sagittal plane 310 is a plane bisecting the object 10 into left and right portions, the coronal plane 320 dividing the object into front and rear portions, and the transverse plane 330 is a plane dividing the object into upper and lower portions. The axis of the object 10 may be defined by a fourth axis (or an X-axis) 4 that is a sagittal axis formed by the intersection of the sagittal plane 310 and the transverse plane 330, a fifth axis (a Y-axis) 5 that is a vertical axis formed by the intersection of the sagittal plane 310 and the coronal plane 320, and a sixth plane (or a Z-axis) 6 that is a transverse axis formed by the intersection of the coronal plane 320 and the transverse plane 330.

To acquire a first transformation relationship between coordinate systems of the first and second medical images, the probe 111 may be positioned on a reference point of the object 10. The reference point of the object 10 may be at least one entity of the object 10. The reference point may be an entity that is easy to identify in the first medical image and remains undeformed despite a respiration of the object 10. For example, the reference point may be a bone that is an entity of the object. The reference point may also be an entity that can be identified by a user's naked eye. For example, the reference point may be a belly button of the object 10. The user may place the probe 111 on the reference point of the object 10. In this case, the probe 111 may be positioned on the reference point by directly contacting the reference point or being separated from the reference point by a certain distance in an upward direction.

Figure 4A:
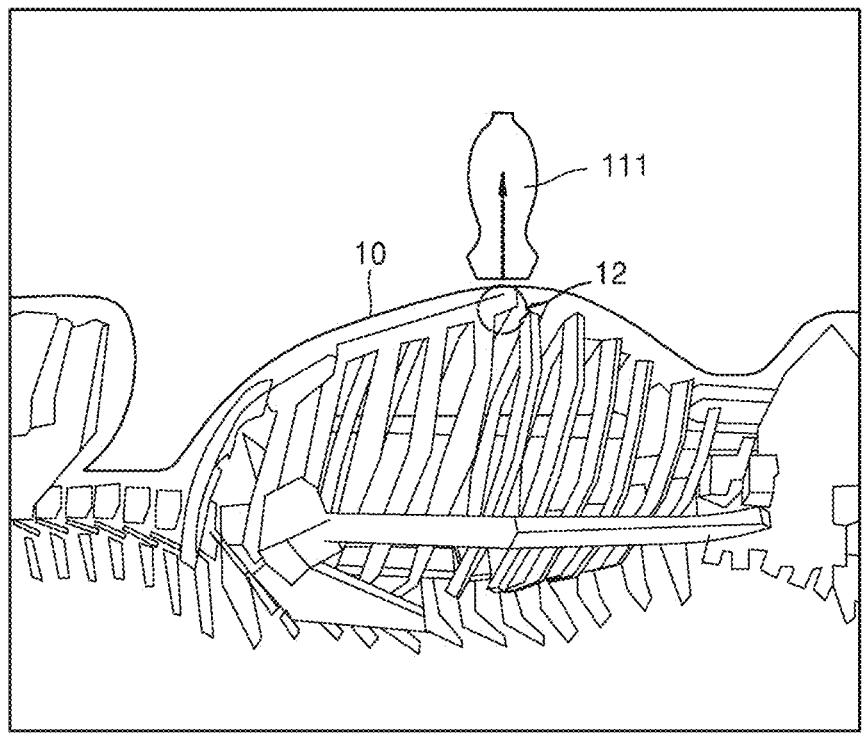
FIGS. 4A and 4B are diagrams for explaining a reference point according to an exemplary embodiment.
Figure 4B:
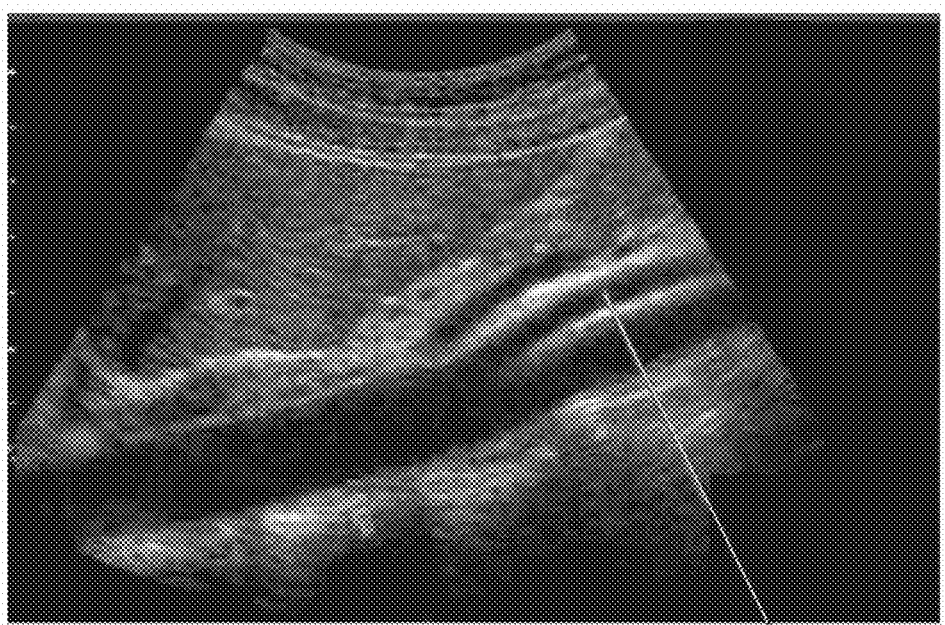

FIGS. 4A and 4B are diagrams for explaining a reference point of an object 10 according to an exemplary embodiment. Referring to FIG. 4A, a user may place a probe 111 on a solar plexus 12 that is an entity of the object 10. The solar plexus 12 may be a reference point of the object 10. In this case, the reference point may be a specific portion of the object 10 preset by, for example, the user.

Alternatively, the user may position the probe 111 on a superior mesenteric artery that is an entity of the object 10. In this case, an image acquired via the probe 111 may include a superior mesenteric artery 13 as shown in FIG. 4B. Thus, the superior mesenteric artery 13 may be a reference point of the object 10. Although the superior mesenteric artery 13 is disposed inside the object 10, the user, e.g., medical personnel such as doctors may easily identify the superior mesenteric artery 13.

Furthermore, the user may position the probe 111 on a reference point of the object 10 so that an axis of the probe 111, i.e., the first axis (1 of FIG. 2) of the probe 111 is parallel to an axis of the object 10, i.e., the fourth axis (4 of FIG. 3). Alternatively, the user may position the probe 111 so that the first through third axes 1 through 3 of the probe 111 are parallel to the fourth through sixth axes 4 through 6 of the object 10, respectively.

When the probe 111 is positioned on a reference point of the object 10, the registration device (140 of FIG. 1) may acquire coordinate information of the reference point from a first medical image acquired via the probe 111. The coordinate information of the reference point is based on a coordinate system of the first medical image.

Information about the reference point, e.g., a shape of the reference point may be prestored in the registration device 140. The probe 111 may acquire the first medical image when being positioned on the reference point of the object 10 and transmit the first medical image to the registration device 140. The registration device 140 may acquire coordinate information of the reference point from the first medical image. For example, if the reference point is a solar plexus, the registration device 140 may define a region of the first medical image representing a bone, extract the solar plexus by using values and number of pixels, and acquire coordinate information of the solar plexus in the coordinate system of the first medical image.

Alternatively, coordinate information of the reference point obtained when the probe 111 is positioned on the reference point may be prestored in the registration device 140. The registration device 140 may acquire coordinate information of the reference point by reading the prestored coordinate information of the reference point.

Furthermore, the registration device 140 may acquire coordinate information of the reference point from a second medical image. In this case, the coordinate information of the reference point is based on a coordinate system of the second medical image. The registration device 140 may acquire the coordinate information of the reference point from the second medical image by using information about a shape of the reference point, etc. or reading prestored coordinate information of the reference point.

For example, if the reference point is a solar plexus and the second medical image is a CT image, a calculator may define a region of the second medical image representing a bone and extract the solar plexus by using values and number of pixels. The calculator may obtain coordinate information of the solar plexus from the coordinate system of the second medical image.

Alternatively, if the second medical image is an MR image, it may be difficult to extract the solar plexus from the second medical image. In this case, when imaging the object 10 to obtain the second medical image, the user may place a marker on a point where the solar plexus of the object 10 is located. The calculator may obtain coordinate information of the solar plexus by extracting the marker from the second medical image. Alternatively, the registration device 140 may estimate coordinate information of the reference point by using another entity that is adjacent to the reference point.

The registration device 140 may also acquire a first transformation relationship between coordinate systems of the first and second medical images by calculating the first transformation relationship between coordinate information of the reference point in the coordinate system of the first medical image and in the coordinate system of the second medical image.

Figure 5:
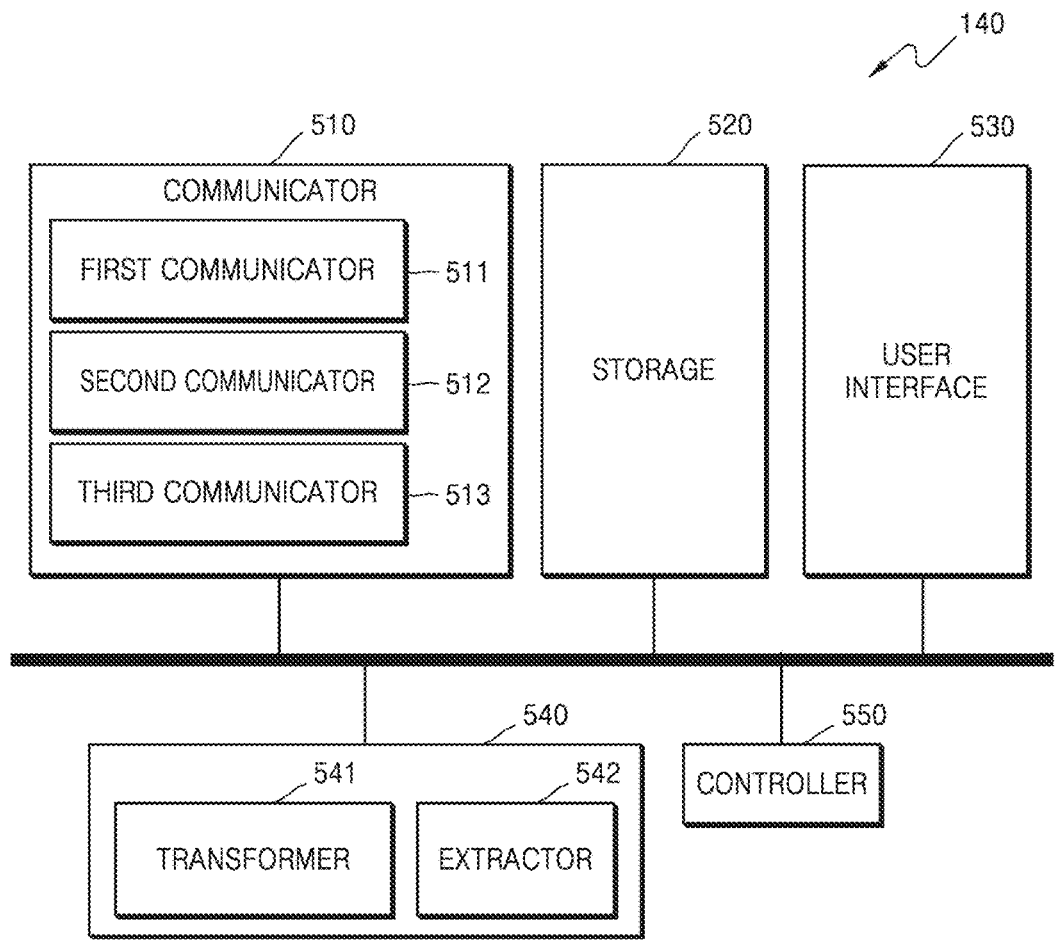
FIG. 5 is a block diagram of a registration device shown in FIG. 1.
Figure 6:
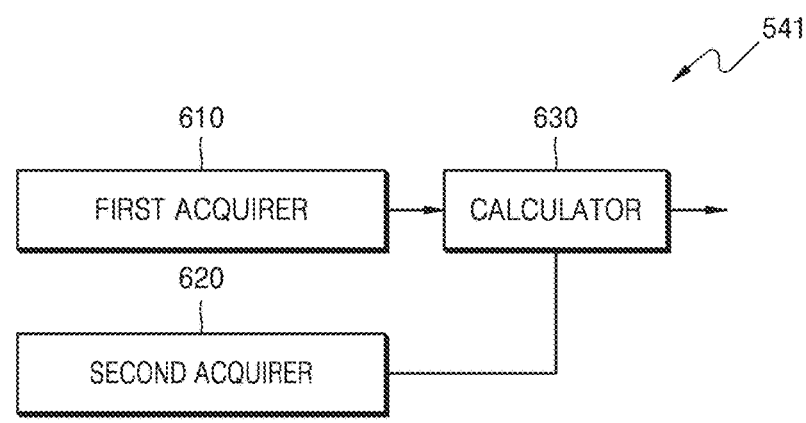
FIG. 6 is a block diagram of a transformer shown in FIG. 5.

FIG. 5 is a block diagram of the registration device 140 shown in FIG. 1, and FIG. 6 is a block diagram of a transformer 541 shown in FIG. 5. Referring to FIG. 5, the registration device 140 may include a communicator 510, a storage 520, a user interface 530, a processor 540, and a controller 550. The components shown in FIG. 5 are not essential components, and the registration device 140 may further include components other than the components shown in FIG. 5.

The communicator 510 may receive first and second medical images from the first and second medical devices 110 and 120, respectively, and at least one of a position and an orientation of the probe 111 from the detection device 130. The communicator 510 may be connected to the first and second medical devices 110 and 120 and the detection device 130 by wire or wirelessly.

The communicator 510 includes a first communicator 511, a second communicator 512, and a third communicator 513. The first communicator 511 may receive in real-time a first medical image being captured by the first medical device 110. The second communicator 512 may connect directly to the second medical device 120 to acquire a second medical image that is captured prior to performing a medical procedure. Alternatively, the second communicator 512 may receive the second medical image via an external storage medium (e.g., a universal serial bus (USB), a compact disk (CD), a digital versatile disk (DVD), etc.) or a network. The storage 520 may store the second medical image received by the second communicator 512.

The third communicator 513 may receive information about a position and an orientation of the probe 111 from the detection device 130. The information about the position and orientation of the probe 111 is coordinate information of the probe 111 in a coordinate system of the detection device 130. The information about the position and the orientation of the probe 111 may be mapped one-to-one with a cross-section of the first medical image received via the first communicator 511. Although it is described that the first medical image and the information about the position and the orientation of the probe 111 are respectively received via different communicators, i.e., the first and third communicators 511 and 513, exemplary embodiments are not limited thereto. In an exemplary embodiment, the first medical image and the information about the position and the orientation of the probe 111 may be received via a single communicator.

The user interface 530 receives an input for manipulating the registration device 140 from a user, and outputs a first medical image, a second medical image, or a registered medical image acquired by the registration device 140. The user interface 530 may include buttons, key pads, switches, dials, or a touch interface that allows the user to manipulate the registration device 140. The user interface 530 may further include a display for displaying an image, and also include a touch screen.

In another exemplary embodiment, the user interface 530 may include an input/output (I/O) port for connecting human interface devices (HIDs). The user interface 530 may also include an I/O port for inputting and/or outputting an image. The user interface 530 may receive a user command for registering first and second medical images when a user places the probe 111 on a reference point and inputs the user command via the user interface 530.

The processor 540 may register a first medical image with a second medical image corresponding to the first medical image and output a registered image to the user interface 530. The processor 540 may include the transformer 541 for transforming coordinate information of the first medical image into coordinate information of the second medical image and an extractor 542 for extracting a cross-section of the second medical image having the coordinate information obtained by the transformation. The transformer 540 may also transform coordinate information of the probe 111 into coordinate information of a cross-section of the first medical image.

Referring to FIG. 6, the transformer 541 may include a first acquirer 610 for acquiring an entity for image registration from a first medical image, a second acquirer 620 for acquiring an entity for image registration from a second medical image, and a calculator 630 for calculating a first transformation relationship between the first and second medical images by aligning acquired entities. The entities acquired by the first and second acquirers 610 and 620 may be identical to or different from each other. According to whether the entities are the same or different, the first transformation relationship may be calculated in different methods.

The first acquirer 610 may acquire an entity from the first medical image. The entity may be at least one of a reference point of an object and an entity other than the reference point which is distinctly identified in the first medical image. For example, if the first medical image is an ultrasound image including a liver, the entity may be an inferior vena cava (IVC) or a diaphragm other than the liver, which is located adjacent to the liver. Alternatively, the entity may be at least one of kidneys, gallbladder, portal vein and hepatic vein, which is located closer to the liver.

The second acquirer 620 may acquire an entity from the second medical image. The entity may be at least one of a reference point of an object and an entity other than the reference point which is distinctly identified in the second medical image. The entity acquired by the second acquirer 620 may be identical to or different from the entity acquired by the first acquirer 610. For example, if an organ of interest is the liver, entities such as the diaphragm, the IVC, etc. may be distinctly visible on both the first medical image, which is, for example, an ultrasound image, and the second medical image, which is, for example, an MR image. Thus, the first and second acquirers 610 and 620 may each acquire the diaphragm or the IVC as the entity other than the reference point, but exemplary embodiments are not limited thereto.

For convenience of explanation, entities other than a reference point which are respectively acquired by the first and second acquirers 610 and 620 are hereinafter called first and second entities, respectively. The second acquirer 620 may acquire the second entity that is different from and adjacent to the first entity. For example, if the first entity is the diaphragm, the second entity may be the liver. In this case, the liver and the diaphragm are not identical entities, but the diaphragm is in contact with a boundary of the liver. Thus, if the diaphragm is considered to be at the boundary of the liver, the first and second medical images may be registered by aligning the diaphragm in the first medical image with the liver in the second medical image.

The calculator 630 may calculate a first transformation relationship between the first and second medical images by using a reference point. For example, the calculator may calculate a first transformation relationship between the first and second medical images by transforming coordinate information of a reference point in the first medical image into coordinate information of the reference point in the second medical image. If the coordinate information of the reference point in the first and second medical images is distinctly indicated, it is possible to register the first and second medical images by using only the first transformation relationship.

The probe 111 may be located on or substantially near the reference point according to a user's skill level. Thus, the registration device 140 may complement the first transformation relationship by using an entity of the object other than the reference point. For example, the calculator 630 may complement the first transformation relationship by using first and second entities in the first and second medical images, respectively.

If the first entity is identical to the second entity, the calculator 630 may complement the first transformation relationship by matching the first and second entities with each other. On the other hand, if the first entity is different from the second entity, the calculator 630 may complement the first transformation relationship by matching a geometry between the first and second entities with a prestored geometry. The geometry between the first and second entities may be prestored.

As described above, the use of the reference point as described above may facilitate calculation of the first transformation relationship between coordinate systems of the first and second medical images compared to using an arbitrary point.

The extractor 542 may obtain a cross-section of the second medical image corresponding to a cross-section of the first medical image from the second medical image. For example, the extractor 542 may transform coordinate information of the cross-section of the first medical image into coordinate information in the coordinate system of the second medical image by using the first transformation relationship and extract a cross-section of the second medical image having the coordinate information obtained by the transformation from the second medical image.

The cross-sections of the first and second medical images are input to the display 150 or the user interface 530 so that the cross-sections are displayed together. The cross-sections of the first and second medical images may be displayed on separate regions, respectively, or may be fused and displayed as a single image.

The transformer 541 may calculate a second transformation relationship between information of a position and an orientation of the probe 111 and coordinate information of a cross-section of the first medical image. In detail, the transformer 541 may calculate information about a position and an orientation of the cross-section of the first medical image from the coordinate information of the cross-section of the first medical image. For example, the position of the cross-section of the first medical image maybe defined as a position of a center of the cross-section, and the orientation of the cross-section may be defined as a normal direction at the center of the cross-section.

The transformer 541 may calculate a second transformation relationship for transforming information about a position and an orientation of the probe 111 that is located on the reference point, i.e., coordinate information of the probe 111 into coordinate information of the cross-section of the first medical image.

If at least one of the position and the orientation of the probe 111 changes, the transformer 541 may calculate coordinate information of the cross-section of the first medical image from changed coordinate information of the probe 111 by using the second transformation relationship.

The controller 550 controls overall operations of the registration device 140. For example, the controller 550 may control the processor 540 to generate an image in response to a user command received via the user interface 530 or by using a program stored in the storage 520. The controller 550 may also control display of an image generated by the processor 540 on the user interface 530 or the display 150.

The operation of the registration device 140 will now be described in more detail with reference to a method of registering medical images as described below. It would be understood by those skilled in the art from the above description that each component in the registration device 140 performs a corresponding operation even if not expressly stated as such.

Figure 7:
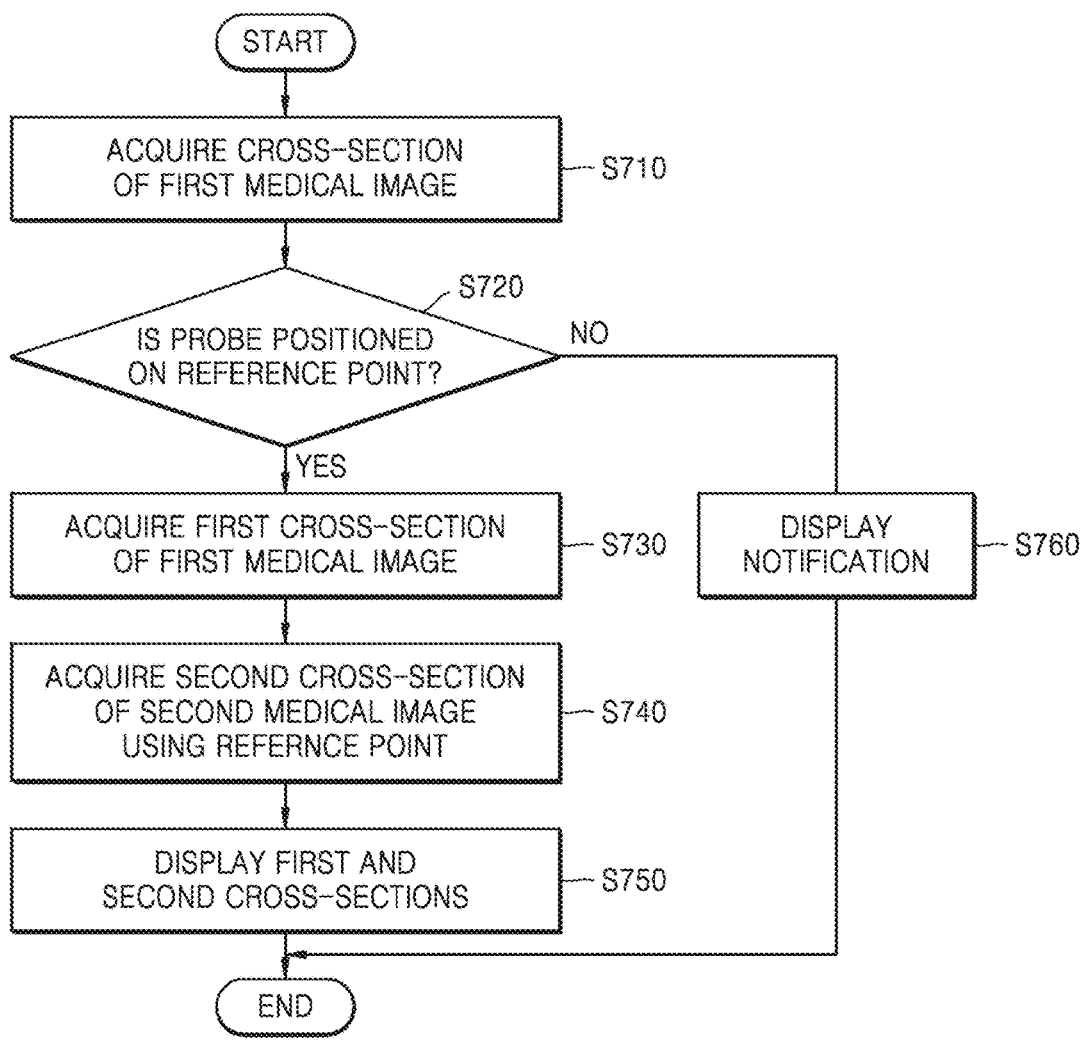
FIG. 7 is a flowchart of a method of registering medical images according to an exemplary embodiment.

FIG. 7 is a flowchart of a method of registering medical images according to an exemplary embodiment. Referring to FIGS. 1, 5, and 7, the registration device 140 may acquire a cross-section of a first medical image from the first medical device 110 (operation S710). For example, the first medical device 110 may generate the cross-section of the first medical image via the probe 111 in real-time and transmit the cross-section to the registration device 140. Although it is described that the first medical device 110 and the registration device 140 are separate devices, the first medical device 110 and the registration device 140 may be integrated into a signal device. In this case, the registration device 140 may acquire the cross-section of the first medical image via the probe 111. That is, the registration device 140 may obtain the cross-section of the first medical image by using a signal received from the probe 111.

The registration device 140 determines if the probe 111 is located on a reference point of an object (operation S720). Prior to the determination, the registration device 140 may provide an indicator for indicating the reference point of the object. If the object has a plurality of reference points, a user may select one of the plurality of reference points.

A user command for positioning the probe 111 on the reference point of the object is hereinafter referred to as a first user command. A user command for image registration is hereinafter referred to as a second user command. The controller 550 of the registration device 140 may determine if the first user command is input by using a result of detection of movement of the probe 111 and/or results of an input via the user interface 530 for receiving a user command.

For example, the user may position the probe 111 on the reference point of the object and inputs the second user command for image registration. When the second user command is input, the controller 550 may determine if coordinate information of the reference point may be obtained from a cross-section of the first medical image acquired at a time point when the second user command is input.

If the cross-section of the first medical image includes the reference point, the controller 550 may determine that the first user command has been input since the coordinate information of the reference point may be obtained from the cross-section of the first medical image.

On the other hand, if the cross-section of the first medical image does not include the reference point, the controller 550 may determine if coordinate information of the reference point may be obtained from an entity in the cross-section of the first medical image. If the coordinate information of the reference point may be obtained from the entity in the cross-section of the first medical image, the controller 550 may determine that the first user command has been input.

For example, if the reference point is a solar plexus and when the cross-section of the first medical image does not include the reference point, i.e., the solar plexus but includes a rib from which the coordinate information of the reference point may be estimated, the controller 550 may determine that the first user command has been input because the coordinate information of the reference point, i.e., the solar plexus may be obtained from coordinate information of the rib. To acquire the coordinate information of the reference point from coordinate information of the entity, a relative position between the entity and the reference point may be prestored in the registration device 140.

Alternatively, the user may position the probe 111 at the reference point of the object for a predetermined time. If the probe 111 is not determined to move for the predetermined time from a result of detection by the detection device 130, the controller 550 may determine if the coordinate information of the reference point may be obtained from the cross-section of the first medical image acquired via the probe 111.

If the cross-section of the first medical image includes the reference point, the controller 550 may determine that the first user command has been input since the coordinate information of the reference point may be obtained from the cross-section of the first medical image. Alternatively, if the cross-section of the first medical image includes an entity from which the coordinate information of the reference point may be estimated, the controller 550 may determine that the first user command has been input.

Before determining that the first user command has been input, the controller 550 may provide a notification inquiring if a user action that positions the probe 111 at the reference point for a predetermined time (e.g., 5 seconds) is intended for image registration. For example, the controller 550 may display a notification indicating "Proceed to Image Registration?" on the display 150 or the user interface 530. If the second user command is input via the user interface 530 or after a lapse of a predetermined time (e.g., 3 seconds), the controller 550 may determine that the first user command has been input. In this case, the reference point may be an entity of the object that remains undeformed despite a respiration of the object or may be identified by the user's naked eye. Examples of the reference point may include a specific bone, a belly button, a superior mesenteric artery, an inferior tip of the liver, and the like. When the probe 111 is positioned on the reference point of the object, a coordinate system of the detection device 130 may be parallel to a coordinate system of the first medical image.

If the probe 111 is positioned on the reference point of the object (operation S720-YES), the registration device 140 may acquire a first cross-section of a first medical image from the first medical device 110 (operation S730). In this case, the first cross-section may be a cross-section of the first medical image including the reference point. For convenience of explanation, operations S720 and S730 are described as separate operations, but may be performed simultaneously. The registration device 140 may acquire a second cross-section of the second medical image from the second medical image by using the reference point (operation S740). The second cross-section of the second medical image corresponds to the first cross-section of the first medical image. The registration device 140 may calculate a first transformation relationship between coordinate systems of the first and second medical images by using the reference point and acquire the second cross-section of the second medical image by using the first transformation relationship.

The registration device 140 may display the first and second cross-sections (operation S750). The registration device 140 may display together the first cross-section received from the first communicator 511 and the second cross-section acquired by the processor 540.

If the probe 111 is not positioned on the reference point of the object (operation S720-NO), the registration device 140 may provide a notification indicating that the first and second medical images cannot be registered (operation S760). For example, the registration device 140 may receive a second user command for image registration when the probe 111 is not positioned on the reference point due to a user's low skill level.

Upon receipt of the second user command, the controller 550 may determine if a first medical image acquired at a time point when the second user command is received includes the reference point. If the first medical image does not include the reference point, the controller 550 may determine that the probe 111 is not positioned on the reference point and provide a notification indicating that the first and second medical images cannot be registered.

If the probe 111 is not positioned on the reference point of the object, the registration device 140 may guide a user to manipulate the probe 111 so that the probe 111 may be positioned on the reference point of the object by providing a notification.

Alternatively, the registration device 140 may acquire a second cross-section of the second medical image from the second medical image by using an entity other than the reference point. The entity may be the most distinctly visible entity among entities in the cross-section of the first medical image or may be an entity represented in a central portion or an upper central portion of the cross-section of the first medical image. Since a general entity-based image registration method may be applied to image registration using an entity instead of a reference point, a detailed description thereof is omitted.

FIG. 8 is a flowchart of a method of calculating a first transformation relationship by using a reference point by the registration device 140, according to an exemplary embodiment.

Referring to FIGS. 1, 6, and 8, the first acquirer 610 may acquire coordinate information of a reference point from a first medical image (operation S810). Coordinate information of a reference point obtained when the probe 111 is positioned on the reference point may be prestored in the registration device 140. In this case, the first acquirer 610 may acquire the coordinate information of the reference point from the first medical image by reading the prestored coordinate information of the reference point from the registration device 140.

The coordinate information of the reference point in the first medical image may be based on a coordinate system of the first medical image. The coordinate system of the first medical image may be predefined. Alternatively, when the probe 111 is positioned on the reference point, the registration device 140 may define the coordinate system of the first medical image by using a first cross-section of the first medical image and a coordinate system of the detection device 130.

If information about a shape of the reference point is stored in the registration device 140, the first acquirer 610 may acquire a first medical image from the first medical device 110 and obtain coordinate information of the reference point from the first medical image by using the information about the shape of the reference point. The coordinate information of the reference point may also be acquired from the first medical image by using other various methods.

The second acquirer 620 may acquire coordinate information of the reference point from a second medical image (operation S820). Coordinate information of the reference point in the second medical image may be prestored in the registration device 140. In this case, the second acquirer 620 may acquire the coordinate information of the reference point from the second medical image by reading the prestored coordinate information of the reference point from the registration device 140. The coordinate information of the reference point in the second medical image is based on a coordinate system of the second medical image.

Alternatively, if information about a shape of the reference point is stored in the registration device 140, the second acquirer 620 may acquire coordinate information of the reference point from the second medical image by using the information about the shape of the reference point. The reference point may be insufficiently clear on the second medical image. In this case, the second acquirer 620 may estimate coordinate information of the reference point by using an entity adjacent to the reference point. Although FIG. 8 shows that operations S820 and S830 are sequentially performed, it is only for convenience of explanation, and operations S820 and S830 may be performed in the reverse order or simultaneously.

Next, the calculator 630 may calculate a first transformation relationship $T_1$ between coordinate systems of the first and second medical images by transforming the coordinate information of the reference point in the first medical image into the coordinate information of the reference point in the second medical image (operation S830). The first transformation relationship $T_1$ may be defined by Equation (1) below:

$$T_1 = x_{MR,0} x_{US,0}^{-1} \qquad (1)$$

where $x_{US,0}$ and $x_{MR,0}$ respectively denote the coordinate information of the reference point in the coordinate systems of the first and second medical images.

In addition, when the probe 111 is positioned on the reference point, a center of the probe 111 may be inaccurately located with respect to a center of the reference point according to a user's skill level. Furthermore, indication of information about the reference point may be insufficiently clear in the first or second medical image. In this case, it may be difficult to accurately calculate a first transformation relationship between coordinate systems of the first and second medical images by using only the reference point. Thus, the registration device 140 according to an exemplary embodiment may complement the first transformation relationship $T_1$ by using an entity of the object other than the reference point.

FIG. 9 is a flowchart of a method of complementing a first transformation relationship according to an exemplary embodiment. Referring to FIGS. 6 and 9, the first acquirer 610 acquires a first entity and coordinate information of the first entity from a first medical image (operation S910). The calculator 630 transforms the coordinate information of the first entity into coordinate information in a coordinate system of a second medical image by using the first transformation relationship (operation S920).

The second acquirer 620 acquires a second entity and coordinate information of the second entity from the second medical image (operation S930). The first and second entities may be distinctly visible on the first and second medical images, respectively. The first and second entities may be identical to or different from each other. Since a general technique for acquiring an entity from a medical image may be applied to acquisition of the first and second entities, a detailed description thereof is omitted. Furthermore, the second acquirer 620 may acquire the second entity from the second medical image in advance and store the acquired second entity. In this case, the second acquirer 620 may load the prestored second entity. Operations S910 and S930 may be performed in the reverse order or simultaneously.

The calculator 630 may complement the first transformation relationship between coordinate systems of the first and second medical images by aligning the first entity having the coordinate information obtained by the transformation with the second entity, thereby acquiring a final first transformation relationship $T_f$ (operation S940). The final first transformation relationship $T_f$ may be defined by Equation (2) below:

$$T_f = T_s T_1 = x_{MR,2} x_{US,1}^{-1} \qquad (2)$$

where $x_{US,1}$ and $x_{MR,2}$ respectively denote the coordinate information of the first entity in the coordinate system of the first medical image and the coordinate information of the second entity in the coordinate system of the second medical image, and $T_1$ and $T_s$ respectively denote a transformation relationship obtained by using a reference point and a complementary transformation relationship acquired by using the first and second entities.

Figure 10:
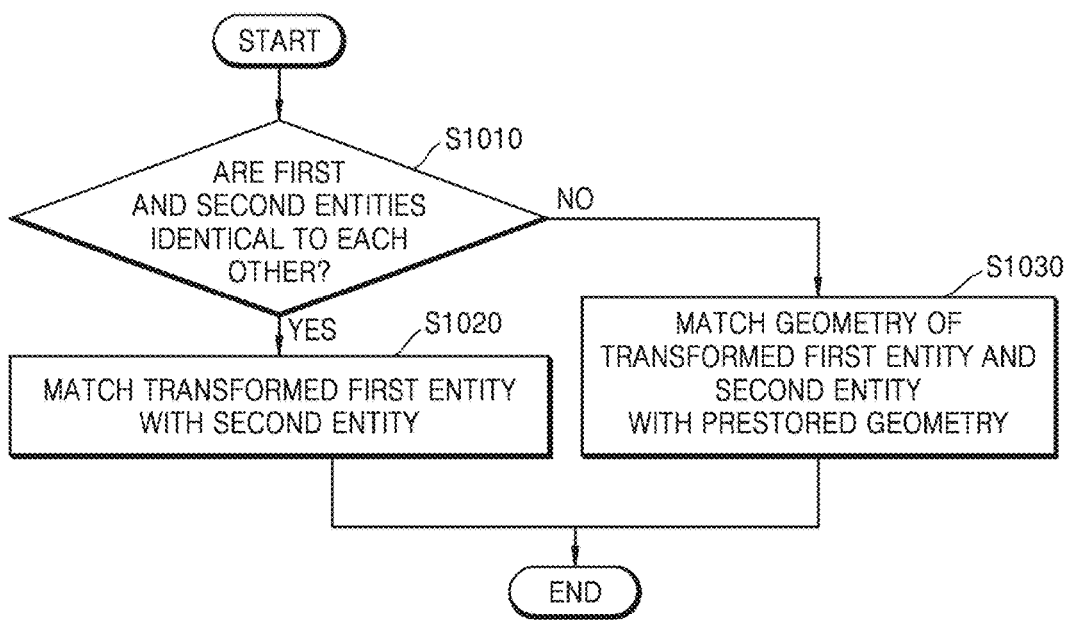
FIG. 10 is a flowchart of a method of aligning a transformed first entity and a second entity according to an exemplary embodiment.

According to whether the first and second entities are identical to or different from each other, the first and second entities may be aligned in different methods. FIG. 10 is a flowchart of a method of aligning first and second entities according to an exemplary embodiment. Referring to FIGS. 1, 6, and 10, the calculator 630 determines if the first and second entities are identical to each other (operation S1010). To do so, the calculator 630 may consider dimensions, radii, etc. of the first and second entities. Alternatively, if the second entity is acquired in advance and stored, the second acquirer 620 may load information about the second entity and acquire a first entity that is identical to the second entity by using the loaded information. In this case, the calculator 630 may determine that the first and second entities are identical to each other. Furthermore, since different entities may be distinctly represented in the first and second medical images, respectively, pieces of information about the first and second entities may be stored in the registration device 140, respectively. If the first and second entities are different from each other, information about geometry between the first and second entities may be prestored in the registration device 140.

If the first and second entities are identical to each other (operation S1010-YES), the calculator 630 may align the transformed first entity with the second entity such that the transformed first entity matches with the second entity (operation S1020).

If the first and second entities are different from each other (operation S1010-NO), the calculator 630 may align the transformed first entity with the second entity such that a geometry between the first transformed entity and the second entity matches a prestored geometry (operation S1030). As described above, the first transformation relationship between the first and second medical images is calculated by matching reference points in the first and second medical images with each other, and is complemented by using the first and second entities. Thus, this method may reduce an image registration error, compared to a case of simply aligning the first and second entities.

Furthermore, if the probe 111 is positioned on the reference point so that an axis of the probe 111 is parallel to an axis of an object, it is easier to calculate the first transformation relationship between the first and second medical images. Since a coordinate axis of the second image is parallel to the axis of the object, a process of controlling coordinate information of the reference points in the first and second images to match with each other may be simplified.

Although it has been described that a reference point is an entity other than first and second entities and a first transformation relationship is calculated using the reference point and complemented using the first and second entities, exemplary embodiments are not limited thereto. The reference point may be the first or second entity. In this case, if the probe 111 is positioned on the first or second entity, the first transformation relationship may be calculated using the first or second entity.

By using the first transformation relationship calculated when the probe 111 is positioned on the reference point or the first transformation relationship further complemented using the first and second entities, a cross-section of the second medical image corresponding to a cross-section of the first medical image may be obtained.

Since the first transformation relationship between coordinate systems of the first and second medical images is calculated using a reference point as described above, image registration using the first transformation relationship may simplify an image registration procedure and reduce an image registration error, compared to a registration procedure of a plurality of images of different modalities captured at an arbitrary position of an object. Furthermore, since the first transformation relationship may be complemented using another entity, it is possible to more accurately acquire the first transformation relationship.

Figure 11:
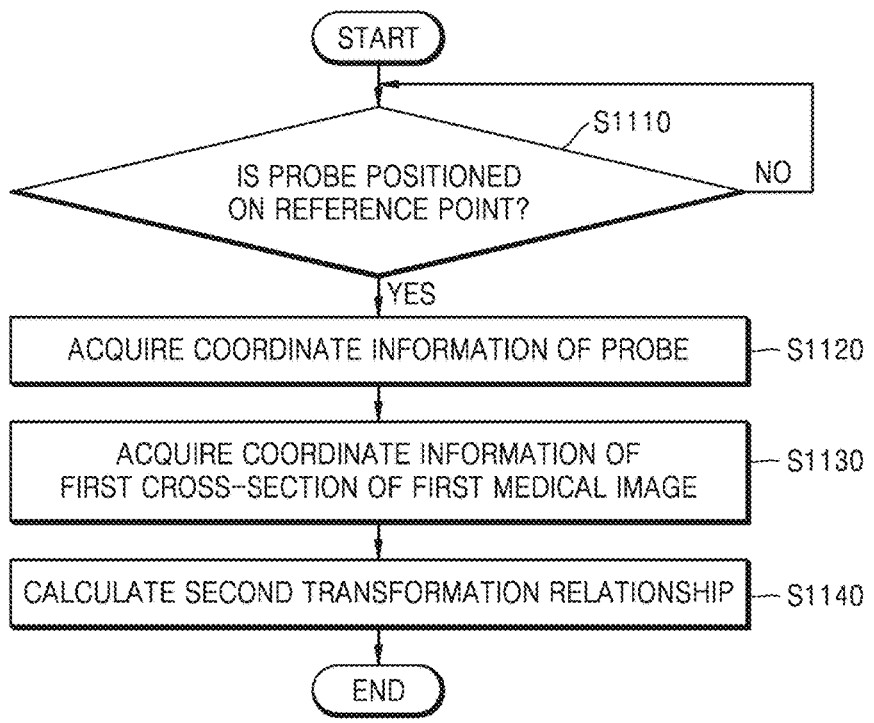
FIG. 11 is a flowchart of a method of calculating a second transformation relationship by using a reference point by a registration device according to an exemplary embodiment.

The registration device 140 according to an exemplary embodiment may acquire a cross-section of a second medical image corresponding to the movement of the probe 111. FIG. 11 is a flowchart of a method of calculating a second transformation relationship using a reference point according to an exemplary embodiment. Referring to FIGS. 1, 6, 11, the registration device 140 determines if the probe 111 is positioned on a reference point of an object (operation S1110). When a user positions the probe 111 on the reference point of the object and inputs a user command for image registration, the controller 550 may determine if the probe 111 is positioned on the reference point of the object. In this case, the reference point may be an entity of the object that remains undeformed despite a respiration of the object or can be identified by the user's naked eye. For example, the reference point may be a specific bone, a belly button, or the like.

If the probe 111 is positioned on the reference point of the object (operation S1110-YES), the registration device 140 may acquire coordinate information of the probe 111 from the detection device 130 (operation S1120). For example, the registration device 140 may acquire information about a position and an orientation of the probe 111 by receiving the information from the detection device 130. In this case, the information about the position and the orientation of the probe 111 may be represented by coordinate information of the probe 111 in a coordinate system of the detection device 130.

The registration device 140 may acquire coordinate information of a first cross-section of a first medical image (operation S1130). The first cross-section of the first medical image is a cross-section acquired via the probe 111 when the probe 111 is positioned on the reference point.

The registration device 140 may calculate a second transformation relationship $T_2$ for transforming the coordinate information of the probe 111 into the coordinate information of the first cross-section of the first medical image (operation S1140). The second transformation relationship $T_2$ is defined by Equation (3) below:

$$T_2 = x_{us,0} x_{p,0}^{-1} \quad (3)$$

where $X_{us,0}$ and $X_{p,0}$ respectively denote the coordinate information of the first cross-section of the first medical image and the coordinate information of the probe 111 when the probe 111 is positioned on the reference point.

The registration device 140 may calculate transformed coordinate information of the first cross-section of the first medical image from the coordinate information of the probe 111 by using the second transformation relationship $T_2$.

Although it is described that the second transformation relationship $T_2$ that is a transformation relationship between the coordinate systems of the detection device 130 and the first medical image is calculated when the coordinate system of the first medical image is preset, exemplary embodiments are not limited thereto. The registration device 140 may set the coordinate system of the first medical image based on the coordinate system of the detection device 130. For example, if the probe 111 is positioned on the reference point, the registration device 140 may define an axis parallel to each of the first through third axes (i.e., 1 through 3 of FIG. 3) as a coordinate axis of the first medical image, and a center of the first cross-section as the origin of the coordinate system of the first medical image. The registration device 140 may calculate a second transformation relationship $T_2$ between the defined coordinate system of the first medical image and the coordinate system of the detection device 130.

Figure 12:
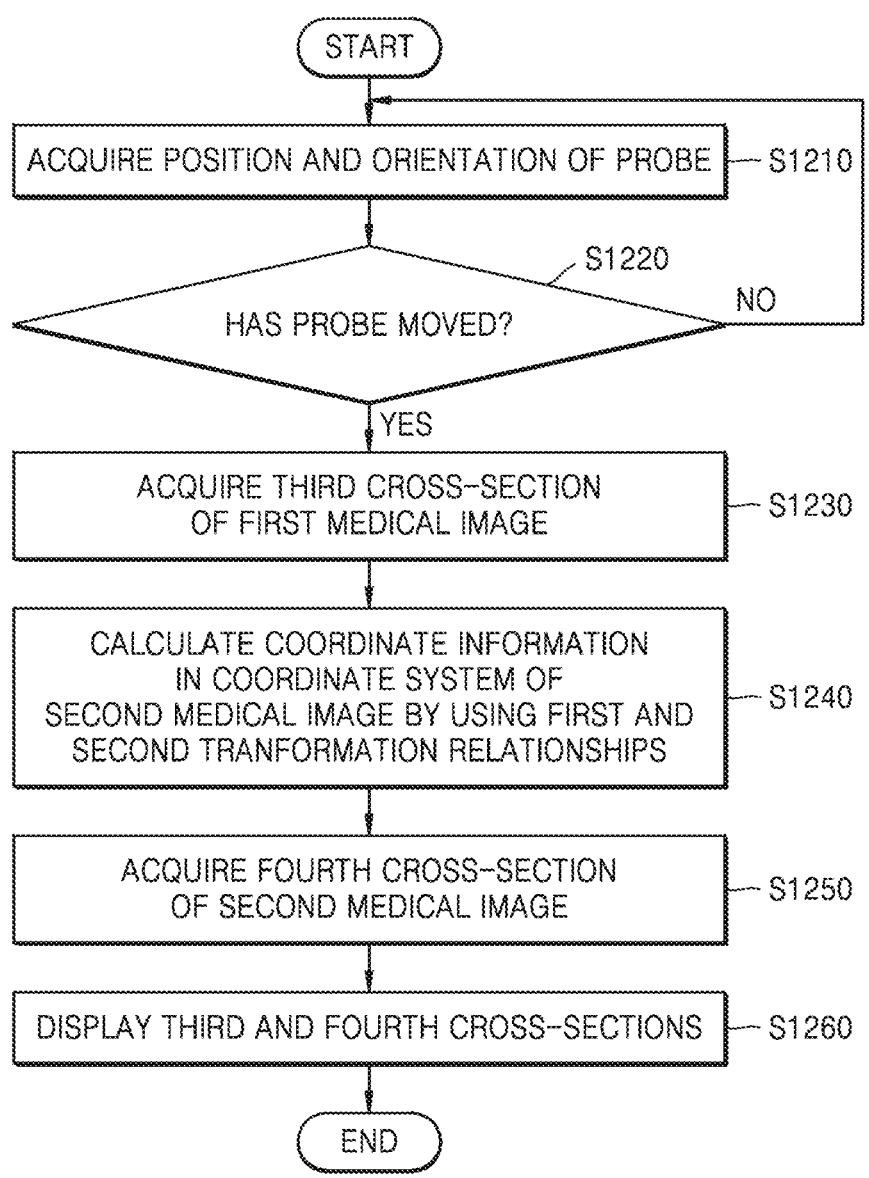
FIG. 12 is a flowchart of a method of acquiring a cross-section of a second medical image corresponding to movement of a probe according to an exemplary embodiment.

FIG. 12 is a flowchart of a method of acquiring a cross-section of a second medical image corresponding to movement of the probe 111 according to an exemplary embodiment. Referring to FIGS. 1, 5, and 12, the registration device 140 acquires information about a position and an orientation of the probe 111 (operation S1210). The registration device 140 acquires the information about the position and the orientation of the probe 111 by receiving the information from the detection device 130 in real-time.

The registration device 140 may determine if the probe 111 has moved (operation S1220). When the probe 111 moves, at least one of a position and a direction of ultrasound waves transmitted to the object or a cross-section of the first medical image may vary. If a result of detection by the detection device 130 shows a change in at least one of the position and the orientation of the probe 111, the registration device 140 may determine that the probe 111 has moved. Although it is described that the registration device 140 determines movement of the probe 111, exemplary embodiments are not limited thereto. The detection device 130 may determine the movement of the probe 111.

The registration device 140 may acquire a third cross-section of the first medical image (operation S1230). The third cross-section may be a cross-section of the first medical image of which at least one of a position and an orientation have been changed due to the movement of the probe 111. The registration device 140 may acquire the third cross-section by receiving the third cross-section from the first medical device 110.

The registration device 140 may calculate coordinate information in a coordinate system of a second medical image, which corresponds to the information about the position and the orientation of the probe 111, by using first and second transformation relationships (operation S1240). As defined by Equation (4) below, the registration device 140 may calculate coordinate information $X_{US,t}$ in the coordinate system of the first medical image corresponding to coordinate information $X_{p,t}$ of the probe 111 by using the second transformation relationship $T_2$, and calculate coordinate information $X_{MR,t}$ in the coordinate system of the second medical image corresponding to the coordinate information $X_{US,t}$ by using the first transformation relationship $T_1$. The first transformation relationship may be a complemented transformation relationship $T_f$, as described above.

$$x_{MR,t} = T_1 T_2 x_{p,t} = T_1 x_{US,t}$$

or $$x_{MR,t} = T_f T_2 x_{p,t} = T_f x_{US,t} \quad (4)$$

The registration device 140 may acquire a fourth cross-section of the second medical image having coordinate information acquired from the second medical image (operation S1250). The extractor 542 may extract the fourth cross-section by extracting a cross-section having coordinate information $X_{MR,t}$ obtained from the second medical image. The third and fourth cross-sections may be the same view of the object.

The registration device 140 may display the third and fourth cross-sections (operation S1260). The third and fourth cross-sections may be displayed on separate regions of a single screen, respectively, or may be displayed on a single region so as to overlap each other. In this manner, a cross-section of the second medical image may be obtained from information about a position and an orientation of the probe 111.

In addition, the registration device 140 may acquire a cross-section of the second medical image from a position and an orientation of the detection device 130 by using a reference point. For example, if the reference point is a bone and a first medical image is an ultrasound image, it may be difficult to obtain coordinate information of the reference point, i.e., the bone from the ultrasound image.

According to an exemplary embodiment, the registration device 140 may also acquire a cross-section of a second medical image from information about a position and an orientation of the probe 111. For example, the registration device 140 may calculate a third transformation relationship for transforming a coordinate system of the detection device 130 into a coordinate system of the second medical image and acquire a cross-section of the second medical image from the information about the position and the orientation of the probe 111 by using the third transformation relationship. Even when coordinate information of the reference point may be acquired from the first medical image, the registration device 140 may acquire the cross-section of the second medical image from the information about the position and the orientation of the probe 111 by using the third transformation relationship.

Figure 13:
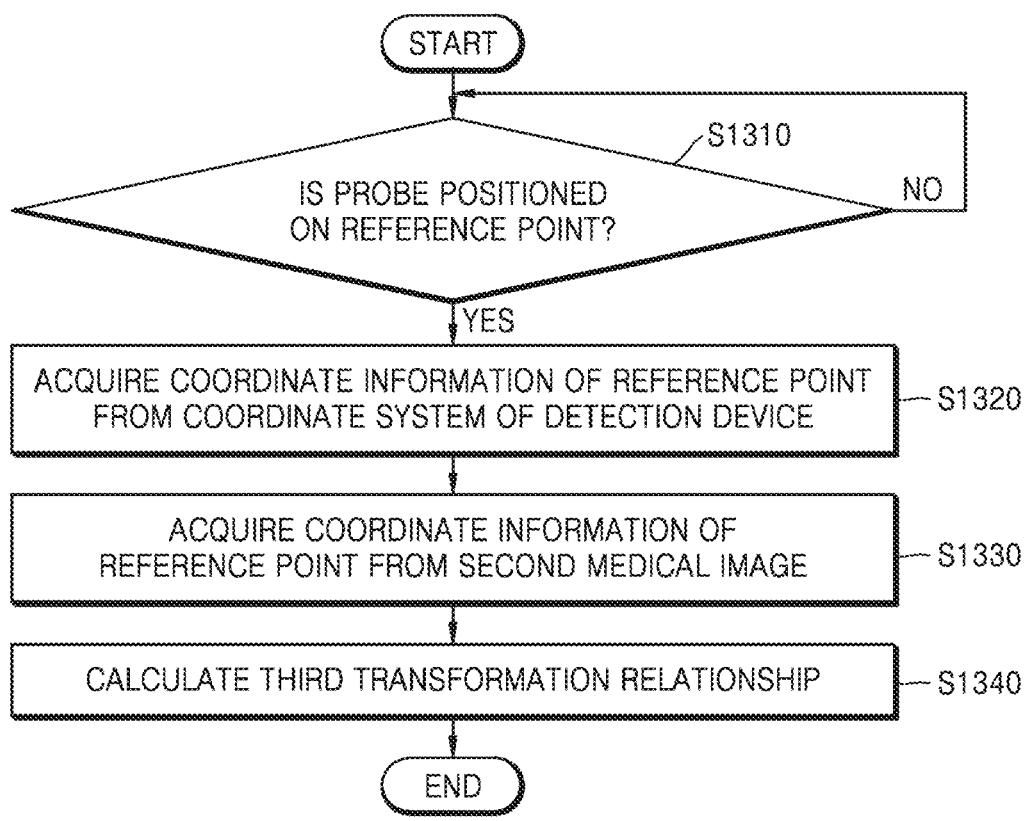
FIG. 13 is a flowchart of a method of calculating a third transformation relationship by using a reference point by a registration device, according to an exemplary embodiment.

FIG. 13 is a flowchart of a method of calculating a third transformation relationship by using a reference point by a registration device, according to an exemplary embodiment.

Referring to FIGS. 1, 5, 6, and 13, the registration device 140 determines if the probe 111 is positioned on a reference point of an object (operation S1310). Before performing operation S1310, the registration device 140 may provide an indicator for indicating the reference point of the object. If there are a plurality of candidates for the reference point of the object, a user may select one of the plurality of candidates as the reference point.

The controller 550 in the registration device 140 may determine if the probe 111 is positioned on the reference point of the object by using at least one of a result of detection of movement of the probe 111 and results of an input via the user interface 530 for receiving a user command. For example, the user may position the probe 111 on the reference point of the object, and input a user command for image registration. When the user command is input, the controller 550 may determine that the probe 111 is positioned on the reference point of the object.

Alternatively, the user may position the probe 111 on the reference point of the object for a predetermined time. If the probe 111 is determined not to have moved for the predetermined time from a result of detection by the detection device 130, the controller 550 may determine that the probe 111 is positioned on the reference point of the object.

Furthermore, the controller 550 may provide a notification inquiring if a user action that positions the probe 111 at a fixed position for a predetermined time (e.g., 5 seconds) is intended for image registration. For example, the controller 550 may display a notification indicating "Proceed to Image Registration?" on the display 150 or the user interface 530. If a user command for image registration is input via the user interface 530 or after a lapse of a predetermined time (e.g., 3 seconds), the controller 550 may determine that the probe 111 is positioned on the reference point of the object. In this case, the reference point may be an entity of the object that remains undeformed despite a respiration of the object or may be identified by the user's naked eye. Examples of the reference point may include a specific bone, a belly button, a superior mesenteric artery, and the like. When the probe 111 is located on the reference point of the object, a coordinate system of the detection device 130 may be parallel to a coordinate system of a second medical image.

If the probe 111 is positioned on the reference point of the object (operation S1310-Y), the processor 540 may acquire coordinate information of the reference point from a coordinate system of the detection device 130 (operation S1320). Coordinate information of the reference point in the coordinate system of the detection device 130 may be prestored in the registration device 140. The processor 540 may acquire the coordinate information of the reference point in the coordinate system of the detection device 130 by reading the prestored coordinate information of the reference point.

Alternatively, the registration device 140 may receive information about a position and an orientation of the probe 111 and estimate the coordinate information of the reference point from the received information. For example, a lookup table (LUT) that defines a relative position between the reference point and the probe 111 that is positioned on the reference point may be prestored in the registration device 140. In this case, the registration device 140 may acquire the coordinate information of the reference point from the information about the position and the orientation of the probe 111 by using the LUT.

In another exemplary embodiment, if a center of the probe 111 is positioned to be in contact with a center of the reference point, the coordinate information of the reference point may be obtained directly from the information about the position and the orientation of the probe 111.

The processor 540 may acquire coordinate information of the reference point from the second medical image (operation S1330). Coordinate information of the reference point in the second medical image may be prestored in the registration device 140. The second acquirer 620 may acquire the coordinate information of the reference point in the second medical image by reading the prestored coordinate information of the reference point. The coordinate information of the reference point in the second medical image is based on the coordinate system of the second medical image.

Alternatively, if information about a shape of the reference point is stored in the registration device 140, the processor 540 may obtain coordinate information of the reference point from the second medical image by using the stored information. In addition, if the reference point is not clearly represented in the second medical image, the second acquirer 620 may estimate coordinate information of the reference point by using an entity that is adjacent to the reference point. Although it is described that the processor 540 acquires coordinate information of the reference point from the second medical image after the processor 540 acquires coordinate information of the reference point from a first medical image, it is only for convenience of explanation, and operations S1320 and S1330 may be performed in the reverse order or simultaneously.

Next, the processor 540 may calculate a third transformation relationship $T_3$ between the coordinate systems of the detection device 130 and the second medical image by transforming the coordinate information of the reference point in the coordinate system of the detection device 130 into the coordinate information of the reference point in the second medical image (operation S1340). The third transformation relationship $T_3$ may be defined by Equation (5) below:

$$T_3 = x_{MR,0} x_{P,1}^{-1} \quad (5)$$

where $x_{P,1}$ and $x_{MR,0}$ respectively denote the coordinate information of the reference point in the coordinate system of the detection device 130 and the coordinate information of the reference point in the coordinate system of the second medical image.

Figure 14:
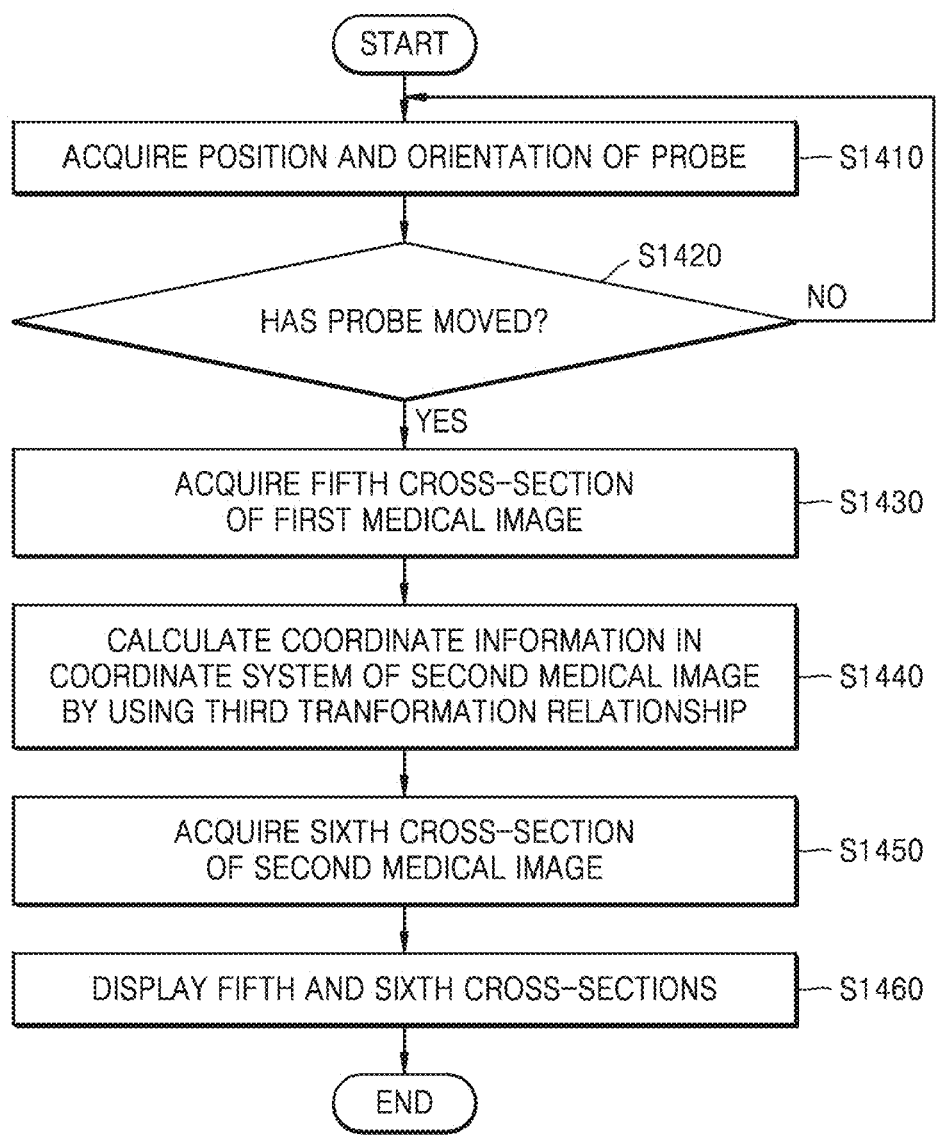
FIG. 14 is a flowchart of a method of acquiring a cross-section of a second medical image corresponding to movement of a probe according to an exemplary embodiment.

The processor 540 may acquire a cross-section of the second medical image corresponding to movement of the probe 111 by using the third transformation relationship $T_3$. FIG. 14 is a flowchart of a method of acquiring a cross-section of a second medical image corresponding to movement of the probe 111 according to another exemplary embodiment. Referring to FIGS. 1 and 14, the registration device 140 acquires information about a position and an orientation of the probe 111 (operation S1410). The registration device 140 acquires information about the position and the orientation of the probe 111 by receiving the information from the detection device 110 in real-time. The information about the position and the orientation of the probe 111 may be represented by coordinate information of the probe 111.

The registration device 140 may determine if the probe 111 has moved (operation S1420). As the probe 111 moves, at least one of a position and a direction of ultrasound waves transmitted to the object or a cross-section of the first medical image may vary. If a result of detection by the detection device 130 shows a change in at least one of the position and the orientation of the probe 111, the registration device 140 may determine that the probe 111 has moved. Although it is described that the registration device 140 determines movement of the probe 111, exemplary embodiments are not limited thereto. The detection device 130 may determine the movement of the probe 111.

The registration device 140 may acquire a fifth cross-section of the first medical image (operation S1430). The fifth cross-section may be a cross-section of the first medical image of which at least one of a position and an orientation have been changed due to the movement of the probe 111. The registration device 140 may acquire the fifth cross-section by receiving the fifth cross-section from the first medical device 110.

The registration device 140 may calculate coordinate information in a coordinate system of a second medical image, which corresponds to the information about the position and the orientation of the probe 111, by using a third transformation relationship (operation S1440). In detail, the registration device 140 may transform the information about the position and the orientation of the probe 111 into coordinate information $X_{p,t}$ of the probe 111 and calculate coordinate information $X_{MR,t}$ in the coordinate system of the second medical image corresponding to the coordinate information $X_{p,t}$ of the probe 111 by using the third transformation relationship, as defined by Equation (6):

$$x_{MR,t} = T_3 x_{p,t} \quad (6)$$

The registration device 140 may acquire a sixth cross-section of the second medical image having coordinate information acquired from the second medical image (operation S1450). The extractor 542 may extract the sixth cross-section by extracting a cross-section having coordinate information $X_{MR,t}$ obtained from the second medical image.

The registration device 140 may display the fifth and sixth cross-sections (operation S1460). The fifth and sixth cross-sections may be displayed on separate regions of a single screen, respectively, or may be displayed on a single region so as to overlap each other. In this manner, a cross-section of the second medical image may be obtained from information about a position and an orientation of the probe 111.

When the probe 111 is positioned on the reference point, a center of the probe 111 may be inaccurately located with respect to a center of the reference point according to a user's skill level. According to an exemplary embodiment, the registration device 140 may complement the third transformation relationship by using an entity of the object other than the reference point. The registration device 140 may complement the third transformation relationship using an entity which is clearly represented in the first medical image.

FIG. 15 is a flowchart of a method of complementing a third transformation relationship according to an exemplary embodiment.

Referring to FIGS. 1, 6, and 15, the first acquirer 610 acquires a first entity and coordinate information of the first entity from a first medical image (operation S1510). The coordinate information of the first entity is based on a coordinate system of the detection device 130. The calculator 630 transforms the coordinate information of the first entity in the coordinate system of the detection device 130 into coordinate information in a coordinate system of a second medical image by using the third transformation relationship (operation S1520).

The second acquirer 620 acquires a second entity and coordinate information of the second entity from the second medical image (operation S1530). In this case, the coordinate information of the second entity is based on a coordinate system of the second medical image. The first and second entities may be distinctly visible on the first and second medical images, respectively. The first and second entities may be identical to or different from each other. Since a general technique for acquiring an entity from a medical image may be applied to acquisition of the first and second entities, a detailed description thereof is omitted.

The calculator 630 may complement the third transformation relationship between the coordinate systems of the detection device 130 and the second medical image by aligning the first entity having the transformed coordinate information obtained by using the third transformation relationship with the second entity, thereby acquiring a final third transformation relationship $T_f$ (operation S1540). The final first transformation relationship $T_f$ may be defined by Equation (7) below:

$$T_{f3} = T_s T_3 = x_{MR,2} x_{P,1}^{-1} \quad (7)$$

where $x_{p,1}$ and $x_{MR,2}$ respectively denote the coordinate information of the first entity in the coordinate system of the detection device 130 and the coordinate information of the second entity in the coordinate system of the second medical image, and $T_3$ and $T_s$ respectively denote a third transformation relationship obtained by using a reference point and a complementary transformation relationship acquired by using the first and second entities.

According to whether the first and second entities are identical to or different from each other, the first and second entities may be aligned in different methods. If the first and second entities are identical to each other, the calculator 630 may complement the third transformation relationship such that the transformed first entity matches with the second entity. On the other hand, if the first and second entities are different from each other, the calculator 630 may complement the third transformation relationship such that a geometry between the transformed first entity with the second entity matches with a prestored geometry.

FIG. 16 is a diagram for explaining a method of displaying an indicator 1610 for indicating a reference point, according to an exemplary embodiment.

Referring to FIGS. 1 and 16, if the registration device 140 is set to an image registration mode in which images of different modalities are registered, the registration device 140 may provide the indicator 1610 for indicating a reference point (e.g., solar plexus 12) via the interface (530 of FIG. 5) or the display 150. The indicator 1610 may be provided in the form of at least one of, for example, a text and an image. In this manner, the user may view the indicator 1610 and position the probe 111 on the reference point (e.g., solar plexus 12).

Figure 17A:
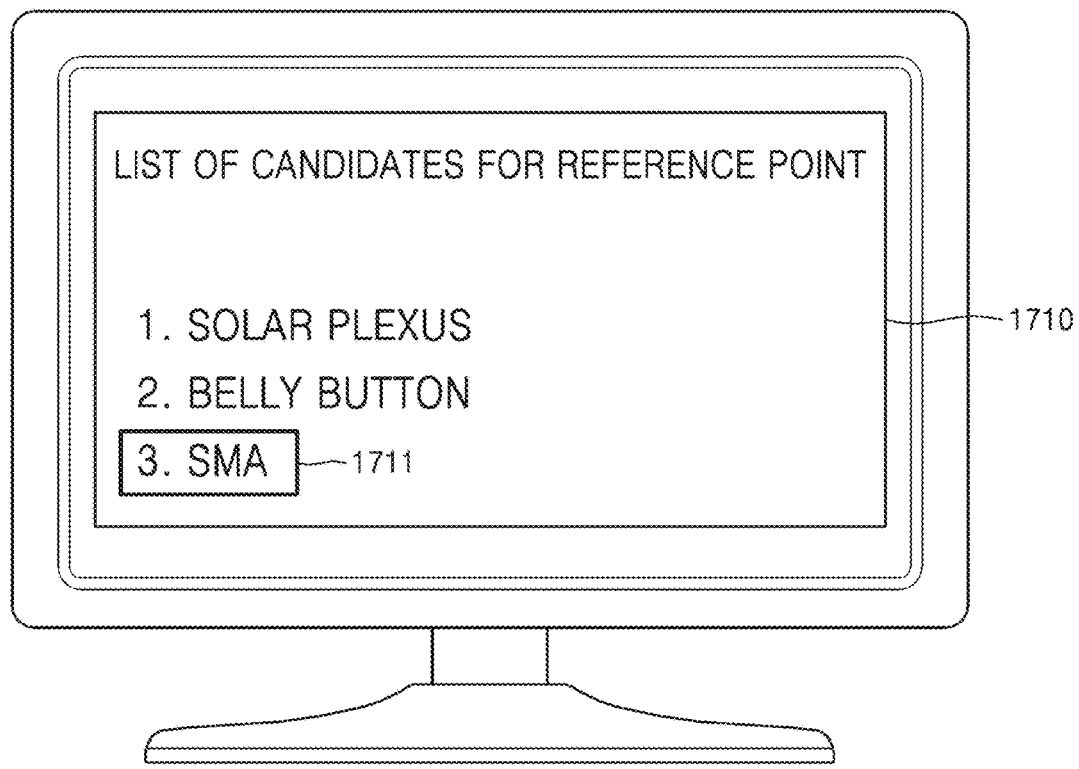
FIGS. 17A and 17B are diagrams for explaining a method of displaying an indicator for indicating a reference point according to an exemplary embodiment.
Figure 17B:
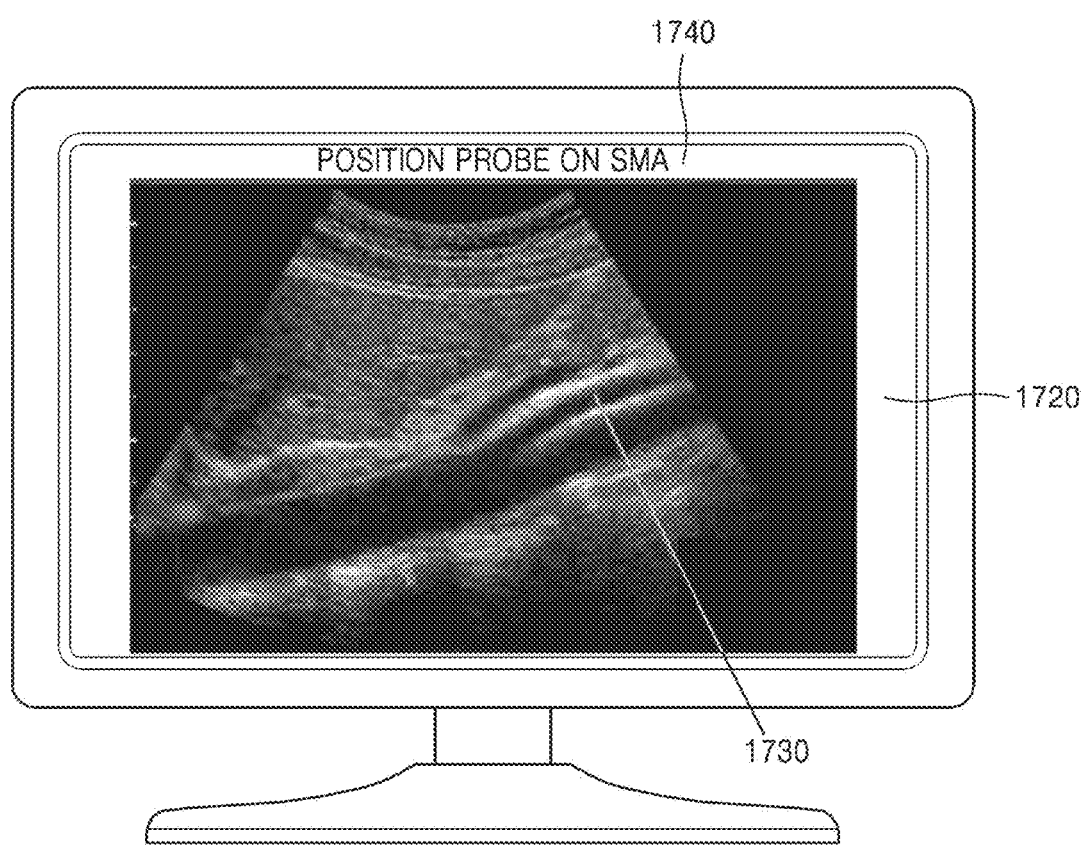

FIGS. 17A and 17B are diagrams for explaining a method of displaying an indicator for indicating a reference point according to another exemplary embodiment.

Referring to FIGS. 1 and 17A, if there are a plurality of reference points for image registration, the registration device 140 may provide a list 1710 of candidates for a reference point. The user may input a user command for selecting a candidate 1711 (e.g., superior mesenteric artery (SMA)) from the list 1710 as the reference point. Referring to FIG. 17B, the registration device 140 may provide an indicator 1720 for indicating the selected reference point 1730, i.e., SMA so that the user may view the indicator 1720 and position the probe 111 on the reference point 1730, i.e., SMA. The indicator 1720 may include a descriptive text 1740 to guide the user to place the probe 111 on the reference point 1730, i.e., SMA.

The methods of registering medical images according to the exemplary embodiments can be recorded as programs that can be executed on a computer and implemented through general-purpose digital computers which can run the programs using a computer-readable recording medium. Data structures described in the above methods can also be recorded on a computer-readable recording medium in various manners. Examples of the computer-readable recording medium include storage media such as magnetic storage media (e.g., read-only memories (ROMs), floppy disks, hard disks, etc.) and optical recording media (e.g., CD-ROMs or DVDs). Furthermore, the computer-readable recording media may include computer storage media and communication media. The computer storage media may include both volatile and nonvolatile and both detachable and on-detachable media implemented by any method or technique for storing information such as computer-readable instructions, data structures, program modules or other data. The communication media may store computer-readable instructions, data structures, program modules, other data of a modulated data signal such as a carrier wave, or other transmission mechanism, and may include any information transmission media.

As described above, exemplary embodiments provide a method of registering an ultrasound image with an image of a different modality than the ultrasound image by using information about a position and an orientation of an ultrasound probe. For example, among organs in a human body, bones are the least deformed, and a person of ordinary skill in the art would be able to easily indicate positions of bones. Furthermore, positions of organs do not change substantially with respect to a position of a bone adjacent to the organs. Thus, according to exemplary embodiments, after placing an ultrasound probe on a designated bone so that an axis of the probe coincides with an axis of a patient, e.g., an axis defined by a patient's head, arms, etc., an ultrasound image and an image of a different modality may be registered with each other by using a position and an orientation of the probe.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for registering medical images, the apparatus comprising:
 a processor configured to acquire, via an ultrasound probe, a first cross-section of a first medical image; and
 a memory configured to store information about a reference point, the reference point corresponding to an entity of an object and being preset prior to acquiring the first cross-section of the first medical image,
 wherein the memory is further configured to store a second medical image, and the processor is further configured to:
  extract areas corresponding to the reference point in the first medical image and in the second medical image by using the information about the reference point, and acquire first coordinate information and second coordinate information of the reference point from a first coordinate system of the first medical image and a second coordinate system of the second medical image, respectively; and
  obtain a second cross-section of the second medical image corresponding to the first cross-section by using the first coordinate information and the second coordinate information of the reference point, and register the first and second medical images with each other based on a transformation relationship between a third coordinate system of a detection device for detecting a position and an orientation of the ultrasound probe and the second coordinate system of the second medical image.

2. The apparatus of claim 1, wherein the processor is configured to register the first medical image with the second medical image in response to a first user command for positioning the ultrasound probe on the reference point of the object.

3. The apparatus of claim 2, further comprising a user interface configured to receive a user command,
 wherein the processor is further configured to determine that the first user command is input based on at least one from among a detection of movement of the ultrasound probe and receipt of the user command via the user interface.

4. The apparatus of claim 3, wherein, when a second user command for image registration is input via the user interface and the first coordinate information of the reference point is obtainable from the first cross-section of the first medical image, the processor is further configured to determine that the first user command is input.

5. The apparatus of claim 3, wherein, when the ultrasound probe does not move for a predetermined time while the first coordinate information of the reference point is obtainable from the first cross-section of the first medical image, the processor is further configured to determine that the first user command is input.

6. The apparatus of claim 1, wherein the reference point corresponds to at least one of a first entity of the object that remains undeformed despite a respiration of the object and a second entity of the object that is distinguishable by a naked eye of a user in the first medical image or the second medical image.

7. The apparatus of claim 1, wherein the entity comprises at least one of a bone, a belly button, and a superior mesenteric artery.

8. The apparatus of claim 7, wherein the bone is a solar plexus.

9. The apparatus of claim 1, wherein the first cross-section is acquired when an axis of a center of the ultrasound probe is disposed parallel to an axis of the object, the axis of the object being defined at least two of a sagittal plane, a coronal plane, and a transverse plane of the object.

10. The apparatus of claim 9, wherein the axis of the center of the ultrasound probe is parallel to a coordinate axis of the first medical image.

11. The apparatus of claim 9, wherein the axis of the object is parallel to a coordinate axis of the second medical image.

12. The apparatus of claim 1, wherein the processor is configured to
extract the second cross-section from the second medical image by using the transformation relationship.

13. The apparatus of claim 12, wherein the processor is configured to complement the transformation relationship by aligning a first entity in the first medical image with a second entity in the second medical image.

14. The apparatus of claim 12, wherein the processor is configured to acquire third coordinate information and fourth coordinate information of the reference point from the third coordinate system of the detection device and the second coordinate system of the second medical image, respectively, and obtain the transformation relationship for transforming the third coordinate information into the fourth coordinate information.

15. The apparatus of claim 12, wherein the processor is configured to acquire, via the ultrasound probe, a third cross-section of the first medical image corresponding to movement of the ultrasound probe and obtain a fourth cross-section of the second medical image corresponding to the third cross-section of the first medical image by using the transformation relationship.

16. The apparatus of claim 15, wherein the movement of the ultrasound probe comprises a change in at least one of the position and the orientation of the ultrasound probe.

17. A method of registering medical images, the method comprising:
acquiring, via an ultrasound probe, a first cross-section of a first medical image;
storing, in a memory, information about a reference point, the reference point corresponding to an entity of an object and being preset prior to acquiring the first cross-section of the first medical image;
extracting areas corresponding to the reference point in the first medical image and in a second medical image by using the information about the reference point, and acquiring first coordinate information and second coordinate information of the reference point from a first coordinate system of the first medical image and a second coordinate system of the second medical image, respectively;
obtaining a second cross-section of the second medical image corresponding to the first cross-section from the second medical image by using the first coordinate information and the second coordinate information of the reference point; and
registering the first medical image and the second medical image with each other based on a transformation relationship between a third coordinate system of a detection device for detecting a position and an orientation of the ultrasound probe and the second coordinate system of the second medical image.

18. The method of claim 17, wherein the obtaining the second cross-section is performed in response to a user command for positioning the ultrasound probe on the reference point of the object.

19. The method of claim 17, wherein the reference point corresponds to at least one of a first entity of the object that remains undeformed despite a respiration of the object and a second entity of the object that is distinguishable by a naked eye of a user in the first medical image or the second medical image.

20. The method of claim 17, wherein the entity comprises at least one of a bone, a belly button, and a superior mesenteric artery.

21. The method of claim 17, further comprising displaying an indicator for indicating the reference point of the object.

22. The method of claim 17, further comprising:
displaying a list of candidates for the reference point; and
receiving a user command for selecting a candidate from the list as the reference point.

23. A non-transitory computer-readable recording medium having recorded thereon a program, which, when executed by a computer, causes the computer to perform the method of claim 17.

24. An apparatus for registering medical images, the apparatus comprising:
a communicator configured to receive a first medical image and a second medical image, the second medical image having a different modality from that of the first medical image;
a processor configured to register the first and second medical images based on a transformation relationship; and
a memory configured to store information about a reference point, the reference point being an entity of an object and being preset prior to receiving the first medical image and the second medical image,
wherein, with respect to a first cross-section of the first medical image acquired by an ultrasound probe, the processor is further configured to automatically obtain a second cross-section of the second medical image corresponding to the first cross-section, by extracting areas corresponding to the reference point in the first medical image and in the second medical image by using the information about the reference point, and acquiring first coordinate information and second coordinate information of the reference point from a first coordinate system of the first medical image and a second coordinate system of the second medical image, respectively, and
wherein the processor is further configured to obtain the transformation relationship between a third coordinate system of a detection device for detecting a position and an orientation of the ultrasound probe and the second coordinate system of the second medical image.

25. The apparatus of claim 24, wherein the first medical image is captured in real-time and the second medical image is captured before the first medical image.

26. The apparatus of claim 24, wherein the processor is configured to obtain the transformation relationship to transform the position and the orientation of the ultrasound probe to coordinates of the reference point in the second medical image, and extract the second cross-section using the transformation relationship.

27. The apparatus of claim 26, wherein the processor is configured to complement the transformation relationship by matching a first entity in the first medical image to coordinate information of a second entity in the second medical image.

28. The apparatus of claim 26, wherein the processor is configured to complement the transformation relationship by matching a geometry between a first entity in the first medical image and a second entity in the second medical image to a pre-stored geometry.

29. The apparatus of claim 24, wherein the communicator is further configured to extract the second cross-section using the transformation relationship.

30. The apparatus of claim 29, wherein, when coordinates of the ultrasound probe are changed, the processor is configured to obtain a third cross-section of the second medical image by using the transformation relationship.

31. The apparatus of claim 24, further comprising:
a display configured to display the first cross-section of the first medical image and the second cross-section of the second medical image.

32. The apparatus of claim 31, wherein the display is configured to at least one of display the first cross-section and the second cross-section on separate areas of a screen and display an image obtained by fusing the first cross-section and the second cross-section.

* * * * *